US005916879A

United States Patent [19]

Webster

[11] Patent Number: 5,916,879

[45] Date of Patent: Jun. 29, 1999

[54] DNA TRANSCRIPTION UNIT VACCINES THAT PROTECT AGAINST AVIAN INFLUENZA VIRUSES AND METHODS OF USE THEREOF

[75] Inventor: Robert Webster, Memphis, Tenn.

[73] Assignee: St. Jude Children's Research Hospital, Memphis, Tenn.

[21] Appl. No.: 08/747,286

[22] Filed: Nov. 12, 1996

[51] Int. Cl.[6] .......................... A61K 48/00; C12N 15/87; C12N 15/44

[52] U.S. Cl. .......................... 514/44; 435/459; 435/320.1; 536/23.72; 424/209.1; 424/210.1; 424/816

[58] Field of Search .......................... 536/23.72; 514/44; 424/209.1, 816, 199.1, 210.1; 435/320.1

[56] References Cited

PUBLICATIONS

Fynan, E.F. et al. Proc. Natl. Acad. Sci. USA, vol. 90, pp. 11478–11482, 1993.

Fynan, E.F. et al. Int. J. Immunopharmac., vol. 17, pp. 79–83, 1995.

Chambers, T.M. et al. Virology, vol. 167, pp. 414–421, 1988.

Petropoulos, C.J. et al. Journal of Virology, vol. 65, pp. 3728–3737, 1991.

Benton and Davis, *Science,* 196:180 (1977).

Chapman et al., *Nucle. Acids. Res.,* 19:3979–3986 (1991).

Conry et al., *Cancer Res.,* 54:1164–1168 (1994).

Cox et al., *Virol,* 67:5664–5667 (1993).

Davis et al., *Hum. Mole. Genet.,* 2:1847–1851 (1993).

Donnelly et al., Nat.Medicine, 1:583–587 (1995).

Eisenbraun et al., *DNA Cell Biol.,* 12:791–797 (1993).

Fynan et al., *DNA Cell Biol.,* 12:785–789 (1993A).

Grunstein and Hogness, Proc. Natl. Acad. Sci. U.S.A., 72:3961 (1975).

Horimoto, et al., (1995) Virology 213:223–30.

Justewicz, 1995, J. Virol. 69:5414–5421.

Kawaoka et al., Virology, 158:218–227 (1987).

Kawoaka et al., Virology, 139:303–316 (1984).

Montgomery et al., *DNA Cell Bio.,* 12:777–783 (1993).

Ramshaw et al. (1994) Abst. Present. Mol. Approach. Control Infect. Dis., Cold Spring Harbor, New York, p. 116.

Robinson et al., *Vaccine,* 11:957, (1993).

Sedegah et al., *Proc. Natl. Acad. Sci.,* 91:9866–9870 (1994).

Ulmer et al., *Science,* 259:1745–1749 (1993).

Wang et al., *Proc. Natl. Acad. Sci.,* 90:4156–4160 (1993).

Webster et al., *Vaccine,* 12:1495–1498 (1994).

Xiang et al., *Virology,* 199:132–140 (1994).

Xiang et al., *Virology,* 209:564–579 (1994).

Yankauckas et al., *DNA Cell Biol.,* 12:771–776 (1993).

*Primary Examiner*—Mary E. Mosher

*Attorney, Agent, or Firm*—Klauber & Jackson

[57] ABSTRACT

The present invention describes a reliably protective avian vaccine that contains a DNA transcription unit comprising a nucleic acid that encodes a viral protein. This effective and reliable avian vaccine significantly improves upon that which heretofore has been disclosed. The present invention demonstrates that the reliable efficacy found for DNA influenza vaccines, formerly observed in experimental inbred mice, can now be obtained for outbred avian species as well. Methods of use and specific DNA constructs are disclosed.

24 Claims, 5 Drawing Sheets

DNA TRANSCRIPTION UNIT VACCINES THAT PROTECT AGAINST AVIAN INFLUENZA VIRUSES AND METHODS OF USE THEREOF

RESEARCH SUPPORT

The research leading to the present invention was supported in part by the Public Health Service grant AI-08831 from the National Institute of Allergy and Infectious Diseases, and the Cancer Center Support (CORE) grant CA-21765. The government may have certain rights in the present invention. Support for this invention was also provided by the AMERICAN LEBANESE SYRIAN ASSOCIATED CHARITIES.

FIELD OF THE INVENTION

The present invention relates generally to vaccines against influenza viruses, and more particularly to avian vaccines that protect against avian influenza virus. More specifically, the present invention relates to protective DNA vaccines, DNA transcription units in non-replicating vectors that can be used as the active ingredient thereof, and methods of making and using the same.

BACKGROUND OF THE INVENTION

Vaccination with inactivated or attenuated organisms or their products has been shown to be an effective method for increasing host resistance and ultimately has led to the eradication of certain common and serious infectious diseases. The use of vaccines is based on the stimulation of specific immune responses within a host. The use of vaccination to successfully prevent certain diseases, most notably small pox and poliomyelitis, represents a great triumph of immunology.

Unfortunately, effective vaccines have been developed for relatively few of the infectious agents that cause disease in domestic animals and man. This reflects technical problems associated with the growth and attenuation of virulent strains of pathogens. Recently, effort has been placed on the development of subunit vaccines (vaccines that present only selected antigens from a pathogen to the host). Subunit vaccines have the potential for achieving high levels of protection in the virtual absence of side effects. Subunit vaccines also offer the opportunity for the development of vaccines that are stable, easy to administer, and sufficiently cost-effective for widespread distribution.

One particular type of subunit vaccine contains a DNA vector that encodes a specific viral protein. DNA vaccines are described in copending U.S. Ser. No. 08/187,879 filed Jan. 27, 1994, and its corresponding Published International Application WO 95/20660; copending U.S. Ser. No. 08/009,833, filed Jan. 27, 1993, and copending U.S. Ser. No. 07/855,562, filed Mar. 23, 1992, and their corresponding Published International Application WO 93/19183, all disclosures of which are hereby incorporated by reference in their entireties.

There are numerous advantages of the use of such DNA vectors for immunizations. For example, immunization can be accomplished using any antigen encoded by DNA. Furthermore, the DNA encoded antigens are expressed as "pure" antigens in their native states and have undergone normal host cell modifications.

DNA is easily and inexpensively manipulated, and is stable over a wide range of temperatures either as a dry product or in solution. This technology is valuable not only for the development of vaccines against practically any agent, but furthermore can be used to manipulate the immune response in such varied conditions as cancer or during organ transplantation.

The ability of directly injected DNA, that encodes a viral protein, to elicit a protective immune response has been demonstrated in numerous experimental systems [Conry et al., *Cancer Res.*, 54:1164–1168 (1994)], [Cox et al., *Virol*, 67:5664–5667 (1993)], [Davis et al., *Hum. Mole. Genet.*, 2:1847–1851 (1993)], [Sedegah et al., *Proc. Natl. Acad. Sci.*, 91:9866–9870 (1994)], [Montgomery et al., *DNA Cell Bio.*, 12:777–783 (1993)], [Ulmer et al., *Science*, 259:1745–1749 (1993)], [Wang et al., *Proc. Natl. Acad. Sci.*, 90:4156–4160 (1993)], [Xiang et al., *Virology*, 199:132–140 (1994)]. Studies to assess this strategy in neutralization of influenza virus have used both envelope and internal viral proteins to induce the production of antibodies, but in particular have focused on the viral hemagglutinin protein (HA) [Fynan et al., *DNA Cell. Biol.*, 12:785–789 (1993A)], [Fynan et al., *Proc. Natl. Acad. Sci.*, 90:11478–11482 (1993B)], [Robinson et al., *Vaccine*, 11:957, (1993)], [Webster et al., *Vaccine*, 12:1495–1498 (1994)]. The viral hemagglutinin protein is a glycoprotein that mediates adsorption and penetration of influenza virus, and is a major target for host neutralizing antibodies. Influenza virus hemagglutinin proteins exhibit fifteen different serological subtypes, HA 1 to HA 15, associated with the fifteen viral subtypes H1-H15 respectively.

Vaccination through directly injecting DNA, that encodes a viral protein, to elicit a protective immune response produces both cell-mediated and humoral responses. This is analogous to results obtained with live viruses [Raz et al., *Proc. Natl. Acad. Sci.*, 91:9519–9523 (1994)], (Ulmer, 1993, supra), (Wang, 1993, supra), (Xiang, 1994, supra). Studies with ferrets indicate that DNA vaccines against conserved internal viral proteins of influenza, together with surface glycoproteins, are more effective against antigenic variants of influenza virus than are either inactivated or subvirion vaccines [Donnelly et al., *Nat.Medicine*, 6:583–587 (1995)]. Indeed, reproducible immune responses to DNA encoding nucleoprotein have been reported in mice that last essentially for the lifetime of the animal [Yankauckas et al., *DNA Cell Biol.*, 12: 771–776 (1993)].

The possibility of species-specific differences in responsiveness to DNA-based vaccines was first raised in studies by Robinson et al. in 1993, showing that direct inoculation of a defective retroviral vector expressing H7 HA could protect chickens against lethal H7 influenza virus challenge (Robinson, 1993, supra). These investigators reported a wide range of protection rates (Fynan, 1993B, supra), (Robinson, 1993, supra), which were on average considerably lower than the generally high responsiveness observed for mice (Fynan, 1993B, supra). These results show that results obtained for experimental inbred mice cannot necessarily be extrapolated to outbred chickens.

Variable results reported by Robinson et al. (Robinson, 1993, supra) for avians could reflect any of a large number of factors that can influence the efficiency of expression of antigen genes and/or the immunogenicity of DNA vaccines. Examples of such factors include the reproducibility of inoculation, construction of the plasmid vector, choice of the promoter used to drive antigen gene expression and stability of the inserted gene in the plasmid. Depending on their origin, promoters differ in tissue specificity and efficiency in initiating mRNA synthesis [Xiang et al., *Virology*, 209:564–579 (1994)], [Chapman et al., *Nucle. Acids. Res.*, 19:3979–3986 (1991)]. To date, most DNA vaccines in mammalian systems have relied upon viral promoters derived from cytomegalovirus (CMV). These have had good efficiency in both muscle and skin inoculation in a number of mammalian species but may not be as effective in avians. Another factor known to affect the immune response elicited by DNA immunization is the method of DNA delivery; parenteral routes can yield low rates of gene transfer and produce considerable variability of gene expression (Montgomery, 1993, supra). High-velocity inoculation of plasmids, using a gene-gun, enhanced the immune responses of mice (Fynan, 1993B, supra), [Eisenbraun et al., *DNA Cell Biol.*, 12: 791–797 (1993)], presumably because of a greater efficiency of DNA transfection and more effective antigen presentation by dendritic cells. In any case, the corresponding state of current avian vaccine methodology can be improved. Indeed, there are no influenza virus vaccines for avians that are approved for use in the United States.

Pathogenic H5 and H7 subtypes of avian influenza virus emerge at irregular intervals and can decimate dense populations of poultry [Easterday et al., *Iowa State Univ. Press*, 532–551 (1991)]. The feasibility of using a vaccine to prevent the spread of the virus will depend on the availability of preparations that induce durable protective immunity. Although available for restricted use, inactivated virus based vaccines are not standardized in terms of HA content [Wood et al., *Avian Dis.*, 29:867–872 (1985)] and generate antibodies to cross-reactive antigens such as nucleoprotein, thereby precluding detection of live virus in the flock. Such a situation prevents the determination of infection before symptoms become apparent, thus significantly hampering any attempt to isolate or destroy infected birds before the disease spreads throughout the flock. Similarly, the use of an another live virus, such as the fowlpox virus, to express an influenza antigen (Ramshaw et al., in "Molecular Approaches To The Control Of Infectious Diseases" Cold Spring Harbor Oct. 5–Oct. 9, 1994 pg. 116, Abstract) results in the infection of the avian flock with that live virus, an alternative that is, for the foreseeable future, unacceptable both in the United States and abroad. Finally, voluntary destruction of entire flocks, as practiced in the past in the United States [Halvorsen et al., *University of Wisconsin*, 33–42 (1992)], can effectively control avian influenza virus infection but only at a great cost. Such solutions are devastating to individual poultry farmers and can best be labeled as an archaic, stop-gap measure.

The last outbreak of highly pathogenic H5N2 avian influenza in the United States occurred in domestic chickens and turkeys in Pennsylvania in 1983–84, with devastating effects on the poultry industry [Bean et al., *J. Virol.*, 54: 151–160 (1985)]. The virus was eventually eradicated by quarantine and extermination of over 17 million birds at a direct cost of over 60 million dollars and an indirect cost to the industry of more than 250 million dollars [Horimoto et al., *Virol.*, 213: 223–230 (1995)]. Furthermore, this strategy is not even considered tenable under conditions of widespread infection of avian stocks such as is the case in Mexico and other developing countries. The pathogenic avian virus, A/Chick/Queretaro/95 (H5N2) for example, still persists in Mexico and could spread rapidly to the United States, necessitating some practical means to prevent the spread of virus in this country, as well as abroad. Eradication of the virus by destruction of infected birds in Mexico is not considered a reasonable option by the poultry industry. Therefore, an improved, more effective, and most importantly, reliable avian vaccine that does not contain an inactivated influenza virus, nor any other live or attenuated virus, is required in order to protect commercially important avians against pathogenic influenza viruses. It is in part to the attainment of this objective that the present invention is directed.

SUMMARY OF THE INVENTION

The present invention describes a vastly improved method of immunizing avians against influenza viruses. The invention comprises administering an effective quantity of a vector, containing a DNA transcription unit, whereby avians challenged intranasally either with 100 $LD_{50}$ of pathogenic influenza virus or with 100 $ID_{50}$ of non-pathogenic influenza virus are protected. The DNA transcription unit minimally includes a nucleic acid encoding an antigen from an influenza virus subtype operatively linked to a DNA promoter. As is true for all embodiments of the present invention, the vector is neither a live or attenuated virus, nor an inactivated influenza virus.

The antigen can be a nucleic acid encoding any influenza virus protein, combinations thereof, and modifications thereof including a polymerase, protein $PB_2$, $PB_1$, PA, a nucleoprotein, a matrix-protein such as N1 and M2 and a non-structural protein such as N5. When the vaccine is prepared to prevent influenza B, the antigen can be the NB protein. In a preferred embodiment the antigen is a hemagglutinin. In a more preferred embodiment the hemagglutinin is obtained from the influenza virus subtype H5. In the most preferred embodiment the hemagglutinin is obtained from the influenza virus H5N2.

The DNA transcription unit can further comprise a nucleic acid encoding a second antigen from a second influenza virus subtype that can be either operatively linked to the same DNA promoter or operatively linked to a second DNA promoter. Further embodiments are envisioned by the present invention to contain three or more such antigens operatively linked to one or more promoters. In a preferred embodiment at least one of the antigens is a hemagglutinin. In a more preferred embodiment all of the antigens are hemagglutinins. In one embodiment the hemagglutinin antigens are from H9 and H4 influenza virus subtypes. In another embodiment the antigens are from H7 and H5 influenza virus subtypes. In a preferred embodiment having three hemagglutinin antigens, the antigens are from H7, H5, and H4 influenza virus subtypes. In a preferred embodiment having four hemagglutinin antigens, the antigens are from H9, H7, H5, and H4 influenza virus subtypes.

The present invention may be achieved with any of a large number of known DNA promoters such as avian promoters or retrovirus promoters, including avian retrovirus promoters. In one preferred embodiment, the DNA promoter is a cytomegalovirus immediate early promoter. In another preferred embodiment the DNA promoter comprises an avian beta-actin promoter element.

The present invention also includes methods of immunizing an avian. These methods rely on eliciting a protective immune response from an influenza virus subtype by administering to the avian, an effective amount of a vector containing a DNA transcription unit having a nucleic acid that encodes an antigen from the influenza virus subtype which is operatively linked to a DNA promoter. In preferred embodiments the antigen is a hemagglutinin. In one embodiment the protective immune response is from an H4 or H9 influenza virus. In a more preferred embodiment the hemagglutinin is obtained from an H5 or H7 influenza virus. In the most preferred embodiment the influenza virus is from the H5 subtype.

In one embodiment the protective immune response reliably leads to the survival of the avian in greater than 30% of the cases in which the avian is challenged intranasally with 100 $LD_{50}$ of the influenza virus subtype. In a preferred embodiment the protective immune response reliably leads to the survival of the avian in greater than about 60% of the cases in which the avian is challenged intranasally with 100 $LD_{50}$ of the influenza virus subtype. In a more preferred embodiment the protective immune response reliably leads to the survival of the avian in greater than about 75% of the cases in which the avian is challenged intranasally with 100 $LD_{50}$ of the influenza virus subtype. In an even more preferred embodiment the protective immune response reliably leads to the survival of the avian in greater than 95% of the cases in which the avian is challenged intranasally with 100 $LD_{50}$ of the influenza virus subtype. In the most preferred embodiment the protective immune response reliably leads to the survival of the avian in 98–100% of the cases in which the avian is challenged intranasally with 100 $LD_{50}$ of the influenza virus subtype.

Not all influenza virus subtypes are lethal. The present invention includes a vaccine in which a protective immune response reliably leads to the protection of the avian from the non-lethal virus in greater than about 60% of the cases as measured by virus replication assays, in which the avian is challenged intranasally with 100 $ID_{50}$ of the non-lethal influenza virus subtype. In a preferred embodiment the protective immune response reliably leads to protection of the avian in greater than about 75% of the cases in which the avian is challenged intranasally with 100 $ID_{50}$ of the influenza virus subtype. In a more preferred embodiment the protective immune response reliably leads to the protection of the avian in greater than 95% of the cases in which the avian is challenged intranasally with 100 $ID_{50}$ of the influenza virus subtype. In the most preferred embodiment the protective immune response reliably leads to the protection of the avian in 98–100% of the cases in which the avian is challenged intranasally with 100 $ID_{50}$ of the influenza virus subtype. The 100 $ID_{50}$ is one hundred times the dose required to infect 50% of the avians being challenged. All of the types of embodiments described herein for the present invention and exemplified for pathogenic influenza virus subtypes should be understood to be equally applicable to non-lethal influenza virus subtypes except that protection from the virus is evaluated as protection from viral infection and/or viral symptoms, rather than in terms of survival.

The methods of the present invention are considered appropriate for the vaccination of all birds. In preferred embodiments the avian is a chicken, a turkey, a duck, a pheasant, a guinea fowl, a quail, or a goose. In one embodiment the avian is a chicken and the influenza virus subtype is H5N2. In another preferred embodiment the avian is a turkey and the influenza virus subtype is H7N7. In still another embodiment the avian is a turkey and the influenza virus subtype is H5N2.

According to the present invention a vector containing a DNA transcription unit of the present invention may be administered by any of a number of methods including through any parenteral route, by intravenous, intraperitoneal, intradermal, subcutaneous or intramuscular methods or through the use of a gene gun. In a preferred method a gene gun is used.

The amount of DNA administered per dose will vary according to the particular circumstances of any individual case. Generally, the lowest dose that reliably gives maximal protection is preferred. Accordingly, in one embodiment of the methods of the present invention, between 0.01 and 200 $\mu$g of DNA per dose are administered. In preferred embodiments 0.1 to 100 $\mu$g of DNA per dose are administered. In more preferred embodiments 0.5 to 25 $\mu$g of DNA per dose are administered. In the most preferred embodiments 0.75 $\mu$g to 12 $\mu$g of DNA per dose are administered.

In one particular embodiment the DNA promoter is a cytomegalovirus immediate early promoter and the amount of DNA administered is between 1 and 20 $\mu$g. In a preferred embodiment of this type, the amount of DNA administered is between 7.5 and 15 $\mu$g. In another particular embodiment the DNA promoter contains an avian beta-actin element and the amount of DNA administered is between 0.1 and 2.5 $\mu$g. In a preferred embodiment of this type, the amount of DNA administered is between 0.75 and 1.5 $\mu$g.

The present invention also includes methods of immunizing an avian against influenza virus by administering to the avian, an effective amount of a vector containing a DNA transcription unit comprising a nucleic acid that encodes an influenza virus antigen and an immuno-effector that are operatively linked to one or more DNA promoters. Further embodiments are envisioned by the present invention to contain two or more such immuno-effectors operatively linked to one or more promoters. In one embodiment the immuno-effector is a cytokine. In a preferred embodiment the cytokine is interleukin-6. In another preferred embodiment, the cytokine is interferon-$\gamma$. In a more preferred embodiment the antigen is a hemagglutinin. In one embodiment, the antigen and the immuno-effector are each operatively linked to the same promoter for coordinate expression.

The nucleic acid can consist of one contiguous polymer, encoding both the antigen and the immuno-effector, or it can consist of independent nucleic acid segments that individually encode the antigen and the immuno-effector respectively. The nucleic acid encoding the immuno-effector and the antigen may each be either operatively linked to the same DNA promoter or operatively linked to separate DNA promoters. In the latter case, the nucleic acid may be inserted into one vector or the independent nucleic acid segments can be placed into separate vectors. When the antigen and the immuno-effector are placed in separate vectors, the vectors may be administered separately to the subject avian.

In one such embodiment, an effective quantity of a vector containing a DNA transcription unit which minimally includes a nucleic acid encoding an antigen from an influenza virus operatively linked to a DNA promoter is administered to an avian. A supplemental vector is also administered to the avian, wherein the supplemental vector comprises a supplemental DNA transcription unit that comprises a supplemental nucleic acid which encodes an immuno-effector and is operatively linked to a DNA promoter.

The present invention also includes methods of immunizing an avian against more than one subtype of influenza virus. These methods rely on eliciting a protective immune response from one or more influenza virus subtypes by administering to the avian an effective quantity of a vector containing a DNA transcription unit having a nucleic acid that encodes two or more different antigens and that are operatively linked to one or more DNA promoters. Further embodiments are envisioned by the present invention to contain three or more such antigens operatively linked to one or more promoters. In one embodiment at least two of the different antigens are derived from different influenza virus subtypes. In a preferred embodiment at least one of the antigens is a hemagglutinin. In a more preferred embodiment all of the antigens are hemagglutinins. In one such embodiment, the antigens are H7 and H5 operatively linked to the same promoter.

The nucleic acid can consist of one contiguous polymer, encoding all of the different antigens or it can consist of independent nucleic acid segments that encode one or more than one different antigen. The nucleic acid encoding the antigens may be either operatively linked to the same DNA promoter or operatively linked to separate DNA promoters. In the latter case, the nucleic acid may be inserted into one vector or more than one vector. When the antigens are placed in separate vectors, the vectors may be administered separately to the subject avian.

In one embodiment of the present invention the protective immune response reliably leads to the survival of the avian in greater than 30% of the cases in which the avian is challenged intranasally with 100 $LD_{50}$ of at least one of the influenza virus subtypes it has been immunized against. In another embodiment the protective immune response reliably leads to the survival of the avian in greater than 30% of the cases in which the avian is challenged intranasally with 100 $LD_{50}$ of at least two of the influenza virus subtypes it has been immunized against. In yet another embodiment of this type the protective immune response reliably leads to the survival of the avian in greater than 30% of the cases in which the avian is challenged intranasally with 100 $LD_{50}$ of all of the influenza virus subtypes it has been immunized against.

In one preferred embodiment the protective immune response reliably leads to the survival of the avian in greater than about 60% of the cases in which the avian is challenged intranasally with 100 $LD_{50}$ of at least one of the influenza virus subtypes it has been immunized against. In another preferred embodiment the protective immune response reliably leads to the survival of the avian in greater than about 60% of the cases in which the avian is challenged intranasally with 100 $LD_{50}$ of at least two of the influenza virus subtypes it has been immunized against. In yet another preferred embodiment of this type the protective immune response reliably leads to the survival of the avian in greater than about 60% of the cases in which the avian is challenged intranasally with 100 $LD_{50}$ of all of the influenza virus subtypes it has been immunized against.

In another preferred embodiment the protective immune response reliably leads to the survival of the avian in greater than about 75% of the cases in which the avian is challenged intranasally with 100 $LD_{50}$ of at least one of the influenza virus subtypes it has been immunized against. In yet another embodiment the protective immune response reliably leads to the survival of the avian in greater than about 75% of the cases in which the avian is challenged intranasally with 100 $LD_{50}$ of at least two of the influenza virus subtypes it has been immunized against.

In still another embodiment of this type the protective immune response reliably leads to the survival of the avian in greater than about 75% of the cases in which the avian is challenged intranasally with 100 $LD_{50}$ of all of the influenza virus subtypes it has been immunized against. In one such embodiment in which the avian is a chicken, the nucleic acid encodes two different antigens, the first antigen being from H5 and the second antigen being from H7 and the protective immune response reliably leads to the survival of the chicken in greater than 75% of the cases in which the chicken is challenged intranasally with both a 100 $LD_{50}$ of influenza virus subtype H5 and a 100 $LD_{50}$ of influenza virus subtype H7.

In another preferred embodiment the protective immune response reliably leads to the survival of the avian in greater than about 95% of the cases in which the avian is challenged intranasally with 100 $LD_{50}$ of at least one of the influenza virus subtypes it has been immunized against. In yet another preferred embodiment the protective immune response reliably leads to the survival of the avian in greater than about 95% of the cases in which the avian is challenged intranasally with 100 $LD_{50}$ of at least two of the influenza virus subtypes it has been immunized against. In one such embodiment the avian is a chicken, the nucleic acid encodes two different antigens, the first antigen being from H5 and the second antigen being from H7 and the protective immune response reliably leads to the survival of the chicken in greater than 95% of the cases in which the chicken is challenged intranasally with both a 100 $LD_{50}$ of influenza virus subtype H5 and a 100 $LD_{50}$ of influenza virus subtype H7.

In another preferred embodiment of this type the protective immune response reliably leads to the survival of the avian in greater than about 95% of the cases in which the avian is challenged intranasally with 100 $LD_{50}$ of all of the influenza virus subtypes it has been immunized against.

In the most preferred embodiment the protective immune response reliably leads to the survival of the avian in 98 to 100% of the cases in which the avian is challenged intranasally with 100 $LD_{50}$ of at least one of the influenza virus subtypes it has been immunized against. In yet another preferred embodiment the protective immune response reliably leads to the survival of the avian in 98 to 100% of the cases in which the avian is challenged intranasally with 100 $LD_{50}$ of at least two of the influenza virus subtypes it has been immunized against. In one such embodiment the avian is a chicken, the nucleic acid encodes two different antigens, the first antigen being from H5 and the second antigen being from H7 and the protective immune response reliably leads to the survival of the chicken in 98 to 100% of the cases in which the chicken is challenged intranasally with both a 100 $LD_{50}$ of influenza virus subtype H5 and a 100 $LD_{50}$ of influenza virus subtype H7.

In the most preferred embodiment of this type the protective immune response reliably leads to the survival of the avian in 98 to 100% of the cases in which the avian is challenged intranasally with 100 $LD_{50}$ of all of the influenza virus subtypes it has been immunized against.

These and other aspects of the present invention will be better appreciated by reference to the following drawings and Detailed Description.

BRIEF DESCRIPTION OF THE DRAWINGS

FIG. 1 depicts schematic drawings of DNA expression vectors that can be used for immunizations.

FIG. 3 depicts antibody titers in chickens immunized with H5DNA-HA or inactivated whole-virus vaccine and challenged with homologous H5 virus and antigenic variants of H5. The data are the geometric means of the reciprocal of the final dilutions of pooled sera inhibiting four hemagglutinin units of virus. Serum samples were collected on day 21 (3 weeks after primary immunization), on day 31 (10 days after boosting) and 41 (10 days post-challenge).

FIGS. 3A, 3C and 3E depict results following the vaccination of the chickens with the DNA vaccine, whereas In FIGS. 3A and 3B, the vaccinated chickens were challenged with Ty/lr/83 virus; in FIGS. 3C and 3D the vaccinated chickens were challenged with Ck/Penn/83 virus; and in FIGS. 3E and 3F the vaccinated chickens were challenged with Ck/Quert/95 virus. Closed circles, HI titers to Ty/Ire/83 antigen; closed triangles, HI titers to A/Ck/Penn/83 antigen; open circles, HI titers to A/Ck/Quert/95 antigen. Details of the vaccination trials and challenge may be found in Materials and Methods of the Example.

DETAILED DESCRIPTION OF THE INVENTION

Figure 1B:
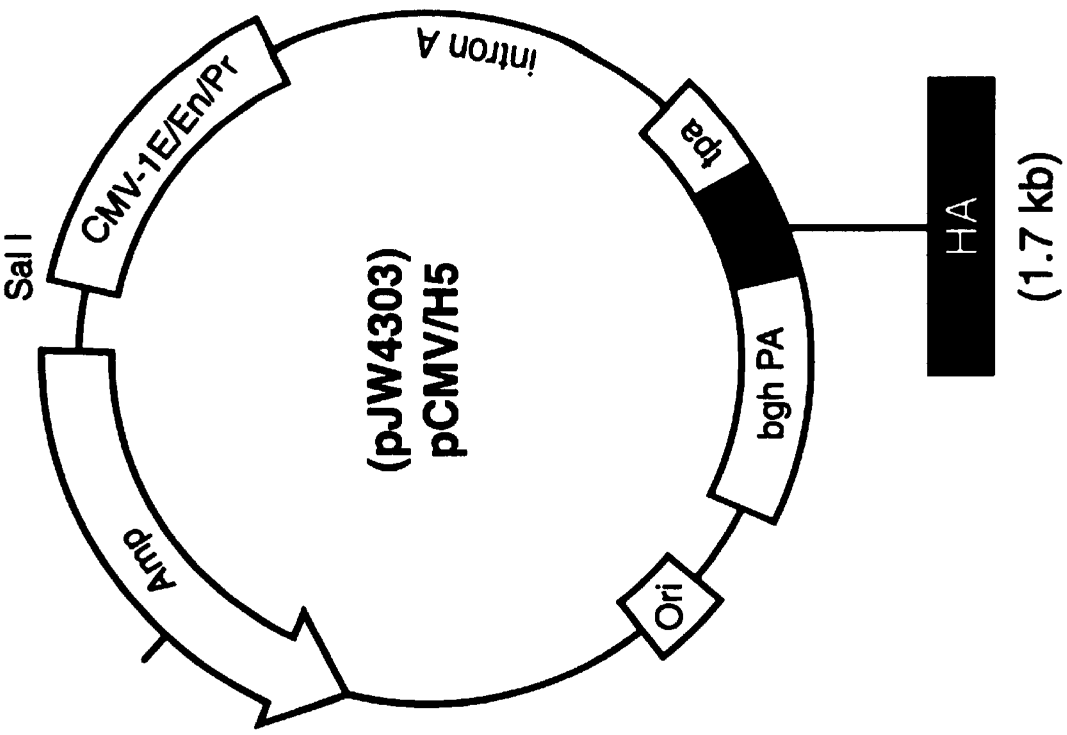
FIG. 1A is a schematic drawing of pCAGGS/MCS/H5 DNA and FIG. 1B is a schematic drawing of pJW4303/H5 DNA. Ori, simian virus 40 (SV 40) origin of replication; CMV-IE/En/Pr, CMV immediate early promoter; CMV-IE/En, CMV immediate early enhancer; H5, hemagglutinin cDNA from A/Ty/Ir/83 (H5H8) influenza virus [Kawaoka et al., *Virology*, 158:218–227 (1987)]; β actin, chicken beta actin promoter; bgh PA, bovine polyadenylation site; rbg PA, chicken beta globulin polyadenylation site; An, simian virus 40 antigen.

The present invention in its broadest aspect, provides a protective avian vaccine that significantly improves upon earlier vaccines by being more effective and more importantly, more reliable. Whereas inoculation with hemagglutinin (HA) expressing DNA affords reliable protection against lethal influenza virus infection in mice, prior to the present invention, the same strategy has yielded variable results in chickens. The present invention achieves a level of efficacy and reliability for a vaccine containing a DNA construct encoding an influenza viral protein, in an avian species, formerly only achieved in mice.

As is true for all embodiments of the present invention, the present invention uses a vector that is neither a live or attenuated virus, nor an inactivated influenza virus. Inactivated influenza virus based vaccines generate antibodies to cross-reactive antigens such as nucleoprotein, thereby precluding detection of live virus in the flock. This hampers the identification of avians that either are infected by or carry influenza virus from healthy vaccinated birds, thereby severely hindering efforts to quarantine or destroy a limited group of infected birds prior to the widespread infection of the flock. Similarly, the use of a live virus, such as the fowlpox virus, to express an influenza antigen results in the infection of the avian flock with that live virus, an alternative th at is, for the foreseeable future, unacceptable both in the United States and abroad.

Therefore, if appearing herein, the terms below set off by quotation marks shall have the definitions as set out herein.

The term "immunizing" refers herein to the production of an immune response in an avian which protects (partially or totally) from the manifestations of infection (i.e., disease) caused by an infectious agent. That is, an avian immunized by the present invention will not be infected or will be infected to a lesser extent than would occur without immunization.

The term "administering" refers herein to the act of placing a DNA transcription unit or other form of vaccine into a subject, such as an avian. This term is used broadly to include administering by a variety of methods, including to a mucosal surface via DNA-containing nose-drops, inhalants, suppositories or by microsphere encapsulated DNA, and methods of inserting microprojectiles into the body e.g., mechanical gene guns or by compressed gasses. The term as used herein is meant to encompass all forms of placing a vaccine into a subject including inoculation.

As used herein, the term administering to the avian "an effective quantity" of a vector is used interchangeably with the term administering to the avian "an effective amount" of a vector and indicates the administering of an effective, and most importantly, a reproducibly effective dose of the vaccine. Depending on the situation, an effective quantity of a vector could reliably lead to protection of greater than 30% of the avians challenged. More preferably, an effective quantity of a vector reliably leads to protection of greater than 60% of the avians challenged. Even more preferably, an effective quantity of a vector reliably leads to protection of greater than 75% of the avians challenged. Yet even more preferably, an effective quantity of a vector reliably leads to protection of greater than 95% of the avians challenged and most preferably an effective quantity of a vector reliably leads to protection of 98–100% of the avians challenged. In tie case of a vaccine against a pathogenic influenza virus, the protection of the vaccine can be determined in terms of the survival of the avian subjects. In the case of a vaccine against a non-pathogenic influenza virus, the protection of the vaccine can be determined in terms of the avian subjects being susceptible versus resistant to infection.

As used herein an "immuno-effector" is a protein that when co-expressed with an influenza viral antigen of the present invention leads to an enhanced immune response to an avian vaccine containing a nucleic acid that encodes the influenza viral protein.

Examples of such heterologous genes for immunomodulatory (or immuno-effector) molecules include, but are not limited to, interferon-α, interferon-γ, interferon-β, interferon-ω, interferon-τ, tumor necrosis factor-α, tumor necrosis factor-β, interleukin-2, interleukin-4, interleukin-6, interleukin-7, interleukin-12, interleukin-15, B7-1 T cell co-stimulatory molecule, B7-2 T cell co-stimulatory molecule, immune cell adhesion molecule (ICAM)-1 T cell co-stimulatory molecule, granulocyte colony stimulatory factor, granulocyte-macrophage colony stimulatory factor, and combinations thereof.

Genetic Constructs Containing Nucleic Acids Encoding Antigens

In accordance with the present invention there may be employed conventional molecular biology, microbiology, and recombinant DNA techniques within the skill of the art. Such techniques are explained filly in the literature. See, e.g., Sambrook, Fritsch & Maniatis, *Molecular Cloning: A Laboratoiy Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

A "DNA transcription unit" is polynucleotide sequence, bounded by an initiation site and termination site, that is transcribed to produce a primary transcript. As used herein, a "DNA transcription unit" includes at least two components: protein-encoding DNA and transcriptional promoter element or elements. Protein-encoding DNA can encode a single antigen or immuno-effector, an antigen and an immuno-effector, or multiple antigens, such as antigens from two or more different proteins of infectious agents, or multiple immuno-effectors, or even multiple antigens and multiple immuno-effectors. The DNA transcription unit can additionally be inserted into a vector which includes sequences for replic ation of the DNA transcription unit. A DNA transcription unit can optionally include additional sequences, such as: enhancer elements, splicing signals, termination and polyadenylation signals, viral replicons and bacterial plasmid sequences. In the present invention, a single type of DNA transcription unit can be administered, or a combination of two or more types of DNA transcription units can be administered.

The DNA transcription unit can be produced by a number of known methods. For example, using known methods, DNA encoding a selected antigen can be inserted into an expression vector. See particularly, Maniatis et al., *Molecular Cloning, A Laboratory Manual*. 2d. Cold Spring Harbor Laboratory Press (1989).

A "vector" is a genetically engineered replicon, such as plasmid, phage or cosmid, to which a heterologous DNA segment is attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, viral sequences, and synthetic DNA sequences. Since the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

Expression of an antigen and/or an immuno-effector may be controlled by any of a number of promoter/enhancer elements known in the art, but these regulatory elements must be functional in the avian host selected for expression. Promoters which may be used to control antigen and/or immuno-effector gene expression include, but are not limited to retrovirus promoters and avian promoters. More specific examples include cytomegalovirus immediate early promoter, an avian promoter such as the chicken beta-actin promoter, both of which are exemplified in the Example, the SV40 early promoter region [Benoist and Chambon, *Nature*, 290:304–310 (1981)], the promoter contained in the 3' long terminal repeat of Rous sarcoma virus [Yamamoto, et al., *Cell*, 22:787–797 (1980)], and the herpes thymidine kinase promoter [Wagner et al., *Proc. Natl. Acad. Sci. U.S.A.*, 78:1441–1445 (1981)].

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. Tile term "translocation signal sequence" is used herein to refer to this sort of signal sequence. Translocation signal sequences can be found associated with a variety of proteins native to eukaryotes and prokaryotes, and are often functional in both types of organisms.

The present invention also relates to cloning vectors containing genes encoding analogs and derivatives of antigens of the present invention, that have the same or homologous antigenic activity. A large number of vector systems known in the art may be used. Possible vectors include, but are not limited to, plasmids or modified viruses, but the vector system must be compatible with the host cell used. The insertion into a cloning vector can, for example, be accomplished by ligating the DNA fragment into a cloning vector which has complementary cohesive termini, However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini, these ligated linkers may comprise specific chemically synthesized oligonucleotides encoding restriction endonuclease recognition sequences.

The necessary transcriptional and translational signals can be provided on a recombinant vector, or they may be supplied by the native gene encoding the influenza viral antigen, such as an influenza viral hemagglutinin and/or its flanking regions.

Genes encoding influenza viral proteins. The present invention contemplates isolation of a gene encoding an influenza viral protein to be used in the invention, including a full length, or naturally occurring form of an influenza viral protein, and any antigenic fragments thereof from any influenza viral source. As used herein, the term "gene" refers to an assembly of nucleotides that encode a polypeptide, and includes cDNA and viral genomic DNA nucleic acids. In a preferred embodiment the influenza viral protein is a hemagglutinin.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., *Cell*, 50:667 (1987)].

Accordingly, the term "sequence similarity" in all its grammatical forms refers to the degree of identity or correspondence between nucleic acid or amino acid sequences of proteins that do not share a common evolutionary origin (see Reeck et al., 1987, supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by aligmnent using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. Thus, the term "corresponding to" refers to the sequence similarity, and not the numbering of the amino acid residues or nucleotide bases.

A gene encoding an influenza viral protein, whether viral genomic DNA or cDNA, can be isolated from any subtype of influenza virus. Methods for obtaining an influenza viral hemagglutinin gene, for example, are well known in the art, as described above (see, e.g., Sambrook et al., 1989, supra).

Accordingly, any influenza virus subtype potentially can serve as the nucleic acid source for the molecular cloning of an influenza viral gene. The DNA may be obtained by standard procedures known in the art from cloned DNA (e.g., a DNA "library") by chemical synthesis, by cDNA cloning, or by the cloning of genomic influenza viral DNA, or fragments thereof, purified from the desired cell (See, for example, Sambrook et al., 1989. supra; Glover, D. M. (ed.), 1985, DNA Cloning: A Practical Approach, MRL Press, Ltd., Oxford, U.K. Vol. I, II).

In the molecular cloning of the gene from influenza viral genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired influenza viral gene may be accomplished in a number of ways. For example, if an amount of a portion of an influenza viral gene or its specific RNA, or a fragment thereof, is available and can be purified and labeled, the generated DNA fragments may be screened by nucleic acid hybridization to the labeled probe [Benton and Davis, *Science*, 196:180 (1977)]; [Grunstein and Hogness, *Proc. Natl. Acad. Sci. U.S.A.*, 72:3961 (1975)]. For example, a set of oligonucleotides corresponding to the partial amino acid sequence information obtained for the influenza viral protein can be prepared and used as probes for DNA encoding the influenza viral gene, or as primers for cDNA or mRNA (e.g., in combination with a poly-T primer for RT-PCR). Preferably, a fragment is selected that is highly unique to an influenza viral gene to be used in the present invention. Those DNA fragments with substantial homology to the probe will hybridize. As noted above, the greater the degree of homology, the more stringent hybridization conditions can be used.

Further selection can be carried out on the basis of the properties of the gene, e.g., if the gene encodes a protein product having the isoelectric, electrophoretic, amino acid composition, or partial amino acid sequence of hemagglutinin protein as disclosed herein. Thus, the presence of the gene may be detected by assays based on the physical, chemical, or immunological properties of its expressed product. For example, CDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for the influenza viral gene product.

An influenza viral gene of the invention can also be identified by mRNA selection, i.e., by nucleic acid hybridization followed by in vitro translation. In this procedure, nucleotide fragments are used to isolate complementary mRNAs by hybridization. Such DNA fragments may represent available, purified influenza viral DNA, or may be synthetic oligonucleotides designed from the partial amino acid sequence information. Immunoprecipitation analysis or functional assays (e.g., tyrosine phosphatase activity) of the in vitro translation products of the products of the isolated mRNAs identifies the mRNA and, therefore, the complementary DNA fragments, that contain the desired sequences.

A radiolabeled influenza viral cDNA can be synthesized using the selected mRNA (from the adsorbed polysomes) as a template. The radiolabeled mRNA or cDNA may then be used as a probe to identify homologous influenza viral DNA fragments from among other genomic influenza viral DNA fragments.

The production and use of derivatives and analogs related to influenza viral gene products are within the scope of the present invention. Influenza viral gene product derivatives can be made by altering encoding nucleic acid sequences by substitutions, additions or deletions that provide for functionally equivalent molecules. Preferably, derivatives are made that have enhanced or increased antigenic activity relative to native influenza viral protein.

Due to the degeneracy of nucleotide coding sequences, other DNA sequences which encode substantially the same amino acid sequence as an influenza viral gene may be used in the practice of the present invention. These include but are not limited to allelic genes, homologous genes from other species, and nucleotide sequences comprising all or portions of influenza viral genes which are altered by the substitution of different codons that encode the same amino acid residue within the sequence, thus producing a silent change. Likewise, the influenza viral gene product derivatives of the invention include, but are not limited to, those containing, as a primary amino acid sequence, all or part of the amino acid sequence of a selected influenza viral protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a cysteine may be introduced a potential site for disulfide bridges with another cysteine. Proline may be introduced because of its particularly planar structure, which induces β-turns in the protein's structure.

The genes encoding an influenza viral protein, derivatives thereof, and analogs thereof can be produced by various methods known in the art. The manipulations which result in their production can occur at the gene or protein level. For example, a cloved influenza viral protein gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of an influenza viral protein, care should be taken to ensure that the modified gene remains within the same translational reading frame as the influenza viral gene, uninterrupted by translational stop signals, in the gene region where the desired activity is encoded.

Additionally, the influenza viral protein-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations eeance the antigenic activity of the mutated influenza viral gene product. Any technique for mutagenesis known in the art can be used, including but not limited to, in vitro site-directed mutagenesis [Hutchinson, C., et al., *J. Biol. Chen.*, 253:6551 (1978)]; [Zoller and Smith, *DNA*, 3:479–488 (1984)]; [Oliphant et al., *Gene*, 44:177 (1986)]; [Hutchinson et al., *Proc. Natl. Acad. Sci. U.S.A.*, 83:710 (1986)], use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich ed., Stockton Press, Chapter 6, pp. 61–70).

The identified and isolated gene can then be inserted into an appropriate DNA transcription unit or cloning vector as described above.

The nucleotide sequence coding for an influenza viral protein, or antigenic fragment, derivative or analog thereof, or a functionally active derivative, including a chimeric protein, thereof, can be inserted into an appropriate vector, i.e., a vector which contains the necessary elements for the transcription and translation of the inserted protein-coding sequence. Such elements are termed herein a "promoter." Thus, the nucleic acid encoding an influenza virus protein of the invention is operationally associated with a promoter in an expression vector of the invention. Both cDNA and genomic sequences can be expressed under control of such regulatory sequences. This vector also preferably includes a replication origin.

Potential chimeric partners for an influenza viral protein, such as hemagglutinin, for example, include additional lectin domains, either from naturally occurring multivalent lectin receptors, such as mannose receptor of macrophages, natural lectins, or other sources. These substitutions and modifications can be made to increase the protective effect of the vaccine containing the DNA transcription unit.

Any of the methods previously described for the insertion of DNA fragments into a vector may be used. These methods may include in vitro recombinant DNA and synthetic techniques and in vivo recombination (genetic recombination).

Immunization

One aspect of the present invention relates to a method of immunizing avianls against an antigen of an infectious agent, e.g., an influenza viral protein, thereby eliciting humoral and/or cell-mediated immune responses which limit the spread or growth of the infectious agent and result in protection against subsequent challenge by the infectious agent. In the method of the present invention, a DNA transcription unit is administered to the avian in whom immunization is desired.

The DNA transcription unit can be administered to an avian in the presence of adjuvants or other substances that have the capability of promoting DNA uptake or recruiting immune system cells to the site of the inoculation. It should be understood that the DNA transcription unit itself is expressed in the host cell by transcription factors provided by the host cell, or provided by a DNA transcriptional unit. A DNA transcription unit can comprise nucleic acids that encode proteins that serve to stimulate the immune response such as a cytokine, proteins that serve as an adjuvant and proteins that act as a receptor.

The antigen can be any antigen or combination of antigens expressed by an influenza virus, or combination of antigens that has been determined to be capable of eliciting a protective response. The antigen or antigens can be naturally occurring, or can be mutated or specifically modified. The antigen or antigens can be of different forms, such as subgroups (clades), subtypes or serotypes of an infectious agent such as hemagglutinins from different serotypes of influenza virus. These antigens may or may not be structural components of a cell or an infectious agent. The encoded antigens can be translation products or polypeptides. The polypeptides can be of various lengths. They can undergo normal host cell modifications such as glycosylation, myristoylation or phosphorylation. In addition, they can be designed to undergo intracellular, extracellular or cell-surface expression. Furthermore, they can be designed to undergo assembly and release from cells.

Vectors containing the nucleic acid-based vaccine of the invention can be introduced into the desired host by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

An avian can be inoculated through any parenteral route or through the use of a gene gun. An avian can be inoculated by a parenteral route by intravenous, intraperitoneal, intradermal, subcutaneous or intramuscular methods, or by a gene gun as exemplified in the EXAMPLE (See, Fynan, 1993B supra). Preferably, when inoculation is performed with a gene gun, the avian subject is de-feathered in the area where the inoculation will occur, e.g., the breast area.

An avian can be inoculated by a mucosal route. The DNA transcription unit can be administered to a mucosal surface by a variety of methods, including DNA-containing nose-drops, inhalants, suppositories or by microsphere encapsulated DNA. For example, the DNA transcription unit can be administered to a respiratory mucosal surface, such as the nares or the trachea or into any surface including the tongue or mucous membrane.

The DNA transcription units are preferably administered in a medium, i.e., an adjuvant, that acts to promote DNA uptake and expression. Preferably, a pharmaceutically acceptable, inert medium is suitable as an adjuvant for introducing the DNA transcription unit into an avian. One example of a suitable adjuvant is alum (alumina gel), though even a saline solution is acceptable. Other possible adjuvants include organic molecules such as squalines, iscoms, organic oils and fats. It should be noted that a vaccine for an avian may contain an adjuvant not appropriate for use in human vaccines.

Immunization as described herein is accomplished with various DNA transcription units (e.g., vectors) that express different proteins. The DNA transcription units described herein are representative of the types of transcription units that can be used in the current invention. The DNA transcription units can encode antigens from a single infectious agent, including antigens from different subgroups (clades) or subtypes of the infectious agent, and can additionally encode antigens from more than one infectious agent.

In one embodiment of the current invention, immunization is achieved with the use of a DNA transcription unit encoding an influenza virus hemagglutinin glycoprotein. In a particular embodiment, DNA expression vectors for the H7 subtype (comprising a DNA transcription unit encoding the H7 subtype hemagglutinin) is used to provide protection against challenge with an H7N7 virus in an avian model. In another particular embodiment, a DNA transcription unit expressing the H5 hemagglutinin is used to immunize against an H5N2 virus. A mixture of DNA transcription units, comprising DNA encoding a variety of antigens from different subgroups (such as subgroups A, B, and C) and/or from different subtypes (such as subtypes 1–15 of subgroup A) of influenza, can also be used in the current invention.

One particular embodiment of the present invention employs the gene-gun delivery of DNA encoding an H5 HA protein that confers complete immune protection to chickens challenged with a lethal H5 virus. In tests of the influence of promoter selection on vaccine efficacy of this particular embodiment, close correlations were obtained between immune responses and the dose of DNA administered, whether a cytomegalovirus (CMV) immediate early or a chicken beta-actin promoter was used. However, at a dose level of 1.0 $\mu$g of DNA, substantially more chickens survived when the vector/promoter transcription unit contained the beta-actin promoter rather than the CMV promoter (100% vs 67%). Very importantly, the HA-DNA vaccine conferred 100% cross-protection against a challenge with lethal antigenic variants that differed from the primary antigen by 15–20% (HA1 nucleotide sequence homology). Overall, the high levels of protection seen with gene-gun delivery of HA-DNA were superior to those achieved with a conventional whole-virus vaccine, having fewer instances of morbidity and death. Thus, this particular embodiment of the present invention provides an attractive means to protect large concentrations of chickens from lethal H5N2 viruses, which continue to circulate in Mexico, as well as in other countries.

An immuno-effector can be co-expressed with an influenza viral antigen of the present invention and thereby enhance the immune response to an avian vaccine containing a nucleic acid that encodes the influenza viral protein antigen. A nucleic acid encoding the immuno-effector may be administered to the avian in a separate DNA transcription unit, operatively linked to a suitable DNA promoter, or alternatively the immuno-effector may be included in a DNA transcription unit comprising a nucleic acid that encodes an influenza virus antigen and an immuno-effector that are operatively linked to one or more DNA promoters. Other embodiments contain two or more such immuno-effectors operatively linked to one or more promoters. The nucleic acid can consist of one contiguous polymer, encoding both the antigen and the immuno-effector or it can consist of independent nucleic acid segments that individually encode the antigen and the immuno-effector respectively. In the latter case, the nucleic acid may be inserted into one vector or the independent nucleic acid segments can be placed into separate vectors. The nucleic acid encoding the inmuno-effector and the antigen may be either operatively linked to the same DNA promoter or operatively linked to separate DNA promoters. Adding such an immuno-effector is known in the art and has been described by Ramshaw et al., (1994) supra. Alternatively, soluble immuno-effector proteins (cytokines, monokines, interferons, etc.) can be directly administered into the avian subject in conjunction with the DNA transcription unit vaccine.

Examples of immuno-effectors include, but are not limited to, interferon-$\alpha$, interferon-$\gamma$, interferon-$\beta$, interferon-$\omega$, interferon-$\tau$, tumor necrosis factor-$\alpha$, tumor necrosis factor-$\beta$, interleukin-2, interleukin-6, interleukin-7, interleukin-12, interleukin-15, B7-1 T cell co-stimulatory molecule, B7-2 T cell co-stimulatory molecule, immune cell adhesion molecule (ICAM)-1 T cell co-stimulatory molecule, granulocyte colony stimulatory factor, granulocyte-macrophage colony stimulatory factor, and combinations thereof.

Vaccination trials may be performed to test protection from either lethal viral infections, as described in the Example, or from non-lethal viral infections. Experimental and control groups of the avians are generally examined together. The avians in the experimental group are administered with a DNA transcription unit on day 0 and then subsequently, e.g., four weeks later, are boosted with a second dose. In preferred embodiments tile two doses are identical. In one particular embodiment, the first dose is administered in the presence of an adjuvant. Some time after the boost, e.g., ten days, the avians in each group are challenged. In one embodiment, the avians are challenged with 100 $LD_{50}$ of a lethal influenza viral strain. The protection of the inoculation is measured as a function of the survival of the challenged avians. In an alternative embodiment, the avians are challenged with 100 $ID_{50}$ of a non-lethal influenza strain. For non-lethal strains, the protection of the inoculation can be measured as a function of the ability of the virus obtained from the challenged avian to replicate in eggs, for example. The avianis are swabbed and the resulting fluid is injected into eggs. The protection of the inoculation can be measured as a function of the viability of the virus, i.e., the ability of the virus to replicate. If the virus grows in the eggs, the avian has not been protected.

The following examples are presented in order to more fully illustrate the preferred embodiments of the invention. They should in no way be construed, however, as limiting the broad scope of the invention.

EXAMPLE

CROSS PROTECTION AMONG LETHAL H5 INFLUENZA VIRUSES INDUCED BY DNA VACCINE TO THE HEMAGGLUTININ

Introduction

Despite the emergence of pathogenic avian influenza virus epidemics at irregular intervals which result in the decimation of dense populations of poultry, prior to the present invention, no effective and more importantly, reliable avian influenza vaccine existed outside of the possible exception of those using inactivated influenza virus or live or attenuated virus. Inactivated influenza virus based vaccines generate antibodies to cross-reactive antigens such as nucleoprotein, thereby precluding detection of live virus in the flock. This hampers the identification of avians that either are infected by or carry influenza virus from healthy vaccinated birds, thereby severely hindering efforts to quarantine or destroy a limited group of infected birds prior to the widespread infection of the flock. Similarly, the use of a live virus, such as the fowlpox virus, to express an influenza antigen results in the infection of the avian flock with that live virus, an alternative that is, for the foreseeable future, unacceptable both in the United States and abroad. Use of an attenuated virus always runs the risk of infection by either poor preparation of attenuated virus samples allowing some virus to remain viable or activation of the virus through recombinant events.

Due to the many experimental variables between studies on experimental mice and chickens, including the fact that the mice are inbred, whereas the chickens are not, it was unclear whether DNA vaccination could reliably produce protective immunity in avians against highly lethal antigenic variants of influenza virus, such as H5. Furthermore, it was highly desirable that such vaccination be at least comparable in protection to the contemporary inactivated virus vaccine. The emergence of A/Chick/Queretaro/95 (H5N2) provided the opportunity to test the efficiency of our H5-DNA vaccine against a challenge by antigenic variants of influenza virus with up to 15% variability in amino acid sequence homology in the antigenic region of HA1. The experiments described here were also designed to compare the role of the promoter element in the DNA vaccine expressing hemagglutinins of influenza strain A/Turkey/Ireland/83 (H5N8) in chickens. The results demonstrate reproducible induction of immune protection against a lethal H5 virus and its antigenic variants, at rates at least comparable to those achieved with a conventional whole-virus inactivated vaccine.

Materials And Methods

Viruses and cells. A/Chick/Queretaro/19/95 (H5N2) (Ck/Quert/95), A/Turkey/Ireland/83 (H5N8) (Ty/Ire/83) and A/Chick/Pennsylvania/1370/83 (H5N2) (Ck/Penn/83) were from the influenza virus repository at St. Jude Children's Research Hospital, Memphis. These viruses were cultivated in the allantoic cavities of embryonated eggs [WHO Collaborating Center for Reference and Research on Influenza, *Center for Disease Control*, (1982)] and handled in the Hospital's USDA-approved BL-3 containment facility. Cos-1 cells were maintained in Dulbecco's minimum essential medium (DMEM) supplemented with antibiotics and 10% fetal bovine serum. Chick embryo fibroblasts were prepared from 10-day-old chick embryos, as described earlier [Taylor et al., *Vaccine*, 6:504–508 (1988)].

Preparation and standardization of inactivated vaccine. Influenza A/Ty/Ire/83 (H5N8) virus was purified by equilibrium density centrifugation through 25% to 75% sucrose gradients [Laver, *Acadenmic Press*, 82–86 (1969)]. Purified virus at the concentration of 40,000 HA units/ml was inactivated with 0.025% formalin at 4° C., resulting in complete loss of infectivity [Katz et al., *J. Infect. Dis*., 160:191–198 (1989)]. The amount of HA per total virus protein was determined by polyacrylamide gel electrophoresis. The bands corresponding to HA on the polyacrylamide gels were stained with Coomassie brilliant blue, and scanned with a Sparc station 2 densitometer (Sun Systems, Foster City, Calif.) and then quantified with the aid of Bioimaging Visage 110 software (Millipore, Bedford, Mass.). The relative HA content of viruses was evaluated by determining the ratio of HA activity to total viral protein content. Protein concentration was estimated by a modification of the Bradford method (Repligen, Cambridge, Mass.).

Serology. HA and hemagglutinin inhibition (HI) assays were perforined with 0.5% chicken red blood cells as previously described (Wood, 1985, supra). Sera from chickens were tested individually after treatment with receptor-destroying enzyme (WHO Collaborating Center for Reference and Research on Influenza, 1982, stipra). HI titers were determined as the reciprocal of the highest serum dilution giving complete inhibition of four hemagglutination units of virus.

Antigenicity and sequence analysis of HA. To investigate the relationship between antigenicity and immunogenicity, HI tests were performed with a panel of monoclonal antibodies prepared against the HA of Ck/Penn/83 (Kawaoka et al., 1987, supra). The amino acid sequence homology among Ck/Penn/83, Ck/Quert/95 and Ty/Ire/83 was analyzed by multiple sequence analysis (GCG pileup).

Figure 1A:
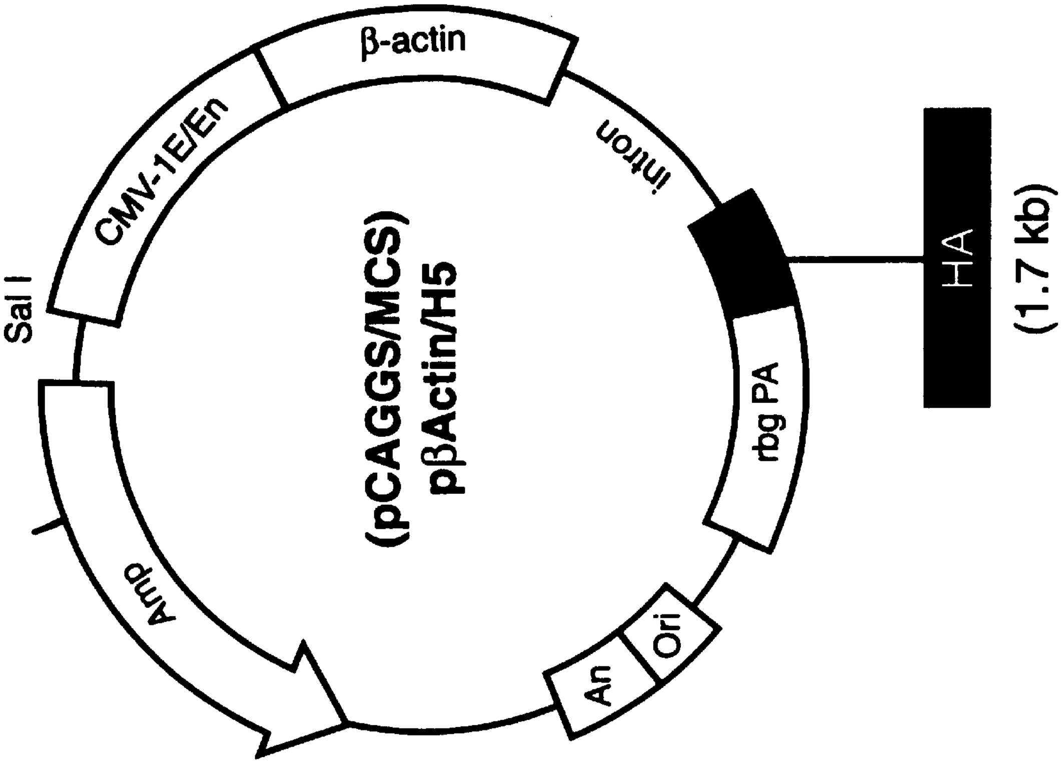

Influenza virus genes and expression vectors. A full-length cDNA copy of the H5HA gene of Ty/Ire/83, designated pTH29, has been cloned [Kawoaka et al., *Virology*, 139:303–316 (1984)]. The full-length HA gene from this clone was obtained by digestion with HindIII-BamHI enzymes and the resulting fragments ligated into a pJW4303 vector provided by B. R. Cullen, Duke University, N.C. [Cullen, *Cell*, 46:973–982 (1986)], under control of a CMV immediate early promoter (pJW4303/h5[Ty/Ir/831]). See FIG. 1B. A plasmid expression vector pCAGGS [Niwa et al., *Gene*, 108:193–200 (1991)] was modified by cloning oligonucleotides containing recognition sites of EcoRI, SacI, ClaI, NsiI, Asp718, SmaI, SphI, XhoI, NheI, and Bg/II between the EcoRI and Bg/II sites (pCAGGS/MCS). The full-length HA gene from the pTH29 clone was also obtained by digestion with ClaI-NheI and ligated into the ClaI-NheI sites of a pCAGGS/MCS vector provide by Y. Kawaoka, (St. Jude Childreni's Research Hospital, Memphis, Tenn.) under the control of a chicken beta-actin promoter, pCAGGS/MCS/H5[Ty/Ir/83]. See FIG. 1A. DNAs were grown in HB101 bacteria and purified on Qiagen plasmid purification columns. DNA concentrations were determined by optical density measurements at 260 nm (Fynan, 1993B, supra).

Transfection. Cos-1 cells or chicken embryo fibroblasts (CEF) were transfected with either pJW4303/H5 (Ty/Ir/83) [pCMV/H5] or pCAGGS/MCS/H5(Ty/Ir/83) [pβ-actin/H5], as described previously [Harms et al., *Human Gene Ther*., 6:1291–1297 (1995)]. Six-well tissue culture plates were seeded with Cos-1 cells ($10^6$/well) and grown until they became about 70% confluent, after which they were washed with 2 ml of reduced serum medium (OPTI-MEM, Life Technologies, Inc., Gaithersburg, Md.), per well. For each transfection (or well), 2 μg of plasmid DNA in 100 μl of OPTI-MEM was mixed with 6 μl of lipofectAMINE in 100 μl of OPTI-MEM. This mixture (0.2 ml) was then incubated at room temperature for at least 30 minutes before it was added to the cells. Three hours later, after incubation at 37° C. in a humidified 5% $CO_2$ incubator, 1 ml/well of medium with 10% fetal calf serum was added to the cells.

Hemadsorption. The expression and biological activity of the influenza virus HA was examined by hemadsorption using chicken RBCs [Kawaoka et al., *Proc. Natl. Acad. Sci*., 85:324–328 (1988)]. At 48 hours post-transfection, the cells were washed and treated with bacterial neuraminidase for 1 hour at 37° C. to remove host cell sialic acid. After 1 hour of incubation, followed by washing to remove neuraminidase, the cells were overlaid at 4° C. with 1% chicken RBCs in isotonic phosphate-buffered saline (PBS). Unbound RBCs were removed 30 minutes later by washing with PBS, after which the cells were fixed with 2% formaldehyde phosphate-buffered saline. Bound RBCs were visualized by staining with Giemsa. Primary chicken embryo fibroblasts were prepared as described (Taylor, 1988, supra), with transfection and hemadsorption performed by standard methods (Kawaoka, 1988, supra).

Indirect immunofluorescence. A total of $2\times10^6$ cells were incubated at 4° C. for 45 minutes with 50 μl of a 1:100 dilution of antibody-containing a pool of Mabs CP34, CP46 and CP59 prepared against the HA of Ck/Penn/83 in ascitic fluid. Cells were washed twice with PBS and incubated for 45 minutes at 4° C. with 100 μl of a 1:20 dilution of FITC-conjugated goat anti-mouse immunoglobulin (Ig). Cells were washed twice with PBS and analyzed in a fluorescence-activated cell sorter (Becton Dickinson; Xiang, 1994, supra).

Gene-gun delivery of DNA. Plasmid DNAs were accelerated into a de-feathered area of breast in 3- to 4-week-old chickens with use of a helium pulse gene gun (Accell; Agracetus, Inc., Middleton, Wis.). Plasmid DNA was affixed to gold particles by adding 10 mg of 0.95 μm gold powder (Degussa, South Plainfield, N.J.) and an appropriate amount of plasmid DNA to a 1.5 ml centrifuge tube containing 50 μl of 0.1 M spermidine. Plasmid DNA and gold were coprecipitated by adding 100 μl of 2.5 M $CaCl_2$ during vortex mixing, after which the precipitate was allowed to settle, washed with absolute ethanol and resuspended in 2.0 ml of ethanol. This suspension as transferred to Mylar sheets and allowed to settle for several minutes, after which the excess ethanol was removed by aspiration. Gold/DNA-coated sheets were dried and stored under vacuum. The energy level for all immunizations was performed with a helium pressure setting of 400 psi.

Dose-response of DNA vaccine and comparison of the CMV and avian β-actin promoter. Dose-response trials in chickens were conducted in a USDA-approved BL3 facility. The bead loading rate used for coating was 0.5 mg of 0.95 micron gold particles per shot. The DNA loading concentration used for coating delivers 0.25 μg, 0.5 μg, 1.0 μg, and 5 μg of DNA per shot respectively. Gene gun inoculations delivered between 0.5 to 1.0 mg of 0.95 micron gold beads depending on whether a single or double shot procedure was used. Additional shots may be employed when necessary without any adverse effects. Five groups of 10 chickens each were inoculated by gene gun with amounts of plasmid DNA ranging from 0.25 μg to 10 μg, in either the pCMV-H5 or the pβ-actin-H5 vector. The groups which received 0.25 μg to 5 μg of DNA were inoculated with single shot beads containing the appropriate amount of DNA. A 10 μg dosage of DNA vaccine was administered in two shots, each shot delivering 5.0 μg of DNA. The energy level for the gene gun had a helium pressure setting of 400 psi. Three weeks after iniunization, the chickens were challenged intranasally with lethal Ty/Ire/83 (H5N8) virus at 100 times the $LD_{50}$.

Immunization and cdallenge infection. Vaccine trials in four groups of chickens were conducted in a USDA-approved BL3 facility. Two separate experimental groups and two separate control groups of chickens were examined. In the first experimental group (n=30), the vaccine consisted of formalin-inactivated whole-virus vaccine. These chickens were primed on day 0 with 10 μg of HA in Freund's incomplete adjuvant, subcutaneously, and four weeks later were boosted with the same dose with vaccine lacking the adjuvant. In the second experimental group (n=30), the chickens were inoculated with 10 μg of DNA encoding H5 using the gene gun methodology, described above, on day 0 and then four weeks later were boosted with the identical dose. In the third group, thirty control chickens received DNA that did not encode the viral hemagglutinin gene. The fourth group consisted of thirty control chickens that were left untreated. Ten days after the boost, and 38 days after the experiment began, the chickens in each of the four groups were divided into three subgroups of 10 birds each, and challenged with 100 $LD_{50}$ of either Ck/Penn/83 (H5N2) or Ck/Queret/95 (H5N2) or Ty/Ire/83 (H5N8).

Results

Expression of hemagglutinin protein in vitro in mammalian vs. chicken cells. The expression and biological activity of the cloned HA gene was assessed by hemadsorption assay. Each of the promoters was able to drive cell membrane expression of the HA protein. To determine the influence of the promoter on the level of HA expression in vitro, we transfected Cos1 and CEF cells with equal amounts of either pCMV-HA or pβ-actin-HA. Two days later, the cells were stained by indirect immunofluorescence with a pool of monoclonal antibodies directed to the H5 hemagglutinin protein and then analyzed by fluorescence-activated cell sorting. Comparable percentages of transfected cells were obtained when either the pCMV-HA (15%) or pβ-actin-HA (12%) vector was introduced into Cos1 cells; however, in CEF cells, the pCMV-HA was expressed at a higher level than the pβ-actin-HA (25% vs 15%).

Antigenic and genetic relationships among H5 viruses. Memory responses developed against one antigen affect subsequent immune responses to antigens that are antigenically and structurally related to the primary antigen. To test the antigenic relationship between Ty/Ire/83 and two H5 subtype variants (Ck/Penn/83 or Ck/Queret/95), the viruses' reactivity with a panel of monoclonal antibodies to the HA region were assessed. The CP25 and CP34 Mabs revealed common epitopes between Ck/Quert/95 and Ck/Penn/83; however, Ck/Quert/95 was less reactive with the seven other monoclonal antibodies tested. Ty/Ire/83 reacted very poorly (10- to 40-fold lower HI titer) with each of the nine test antibodies (Table 1). Ck/Penn/83 and Ty/Ire/83 showed 87% amino acid sequence homology, compared with 89% amino acid sequence homology between Ck/Quert/95 and Ty/Ire/83. Thus, these DNA vaccines permit cross-protection among strains within a subtype having differences as great as 15% in the amino acid sequences of their respective hemagglutinin antigens. This 15% difference is as great a difference as has been documented between two avian influenza virus strains within a particular subtype. Therefore, any DNA vaccine reported herein would have minimally protected inoculated avians from all strains of pathogenic H5 influenza virus that have arisen in the past thirteen years.

TABLE 1

Antigenic and genetic relatedness of H5 influenza viruses by HI analysis with monoclonal antibodies to A/Chicken/Pennsylvania/83 (H5N2) virus.

| Monoclonal antibodies | Ck/Penn/83 | Ck/Quert/95 | Ty/Ire/83 |
|---|---|---|---|
| CP22 | >12800 | 1600 | 160 |
| CP25 | >12800 | >12800 | 160 |
| CP30 | 6400 | <[a] | <[a] |
| CP34 | >12800 | >12800 | 320 |
| CP38 | >12800 | < | < |
| CP55 | >12800 | 1600 | < |
| CP59 | >12800 | 1600 | 640 |
| CP46 | >12800 | 1600 | 320 |
| CP45 | >12800 | < | < |
| % Difference in the amino acid sequence of HA1[b] | 11 | 13 | 0 |

[a]Denotes an HI titer of less than 100.
[b]Based on nucleotide sequence homology of the HA1 region. Hemagglutinins have two functional domains: an antigenic knob, HA1 used in the present analysis, and a stalk, HA2.

Figure 2:
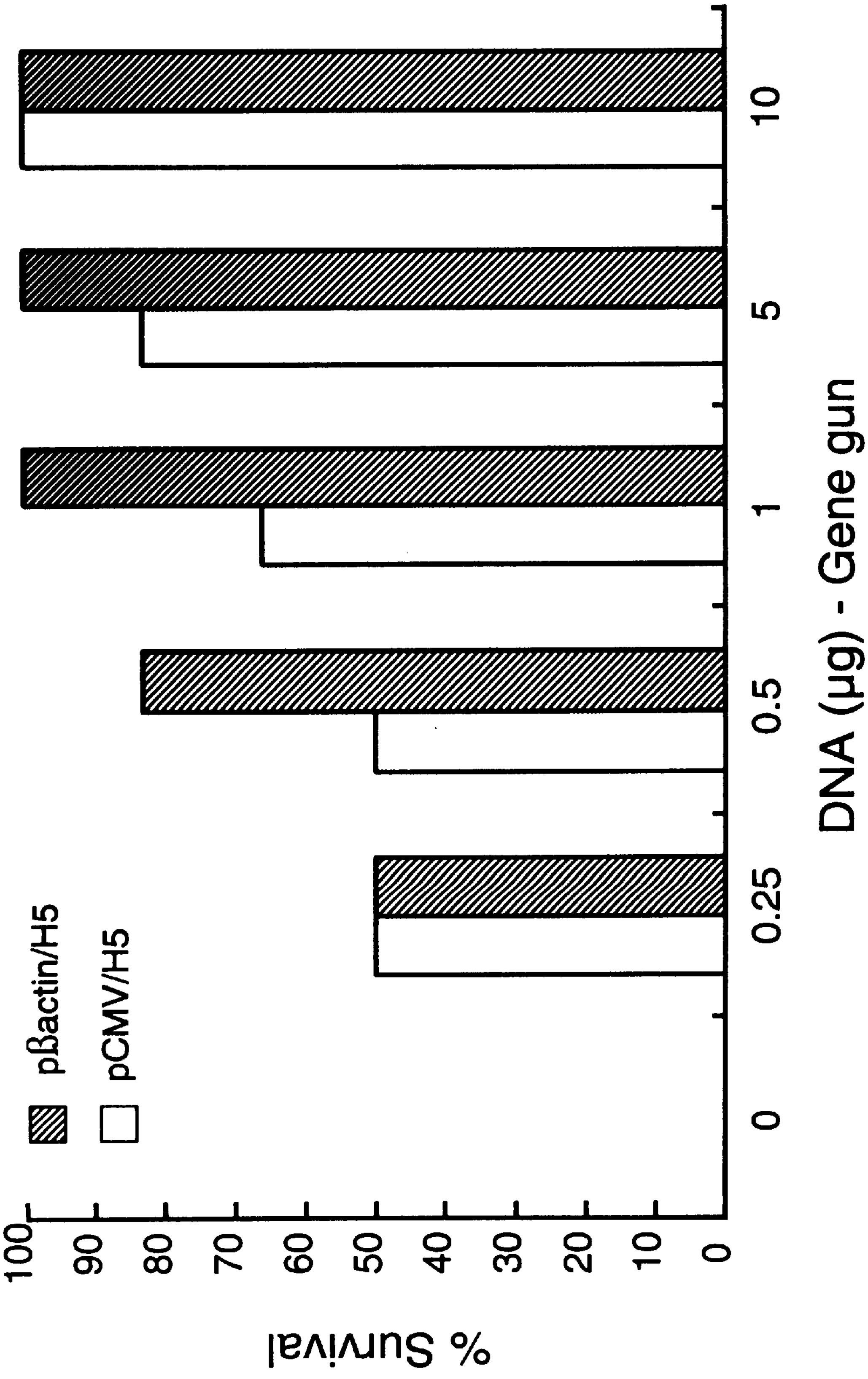
FIG. 2 depicts the dose response of chickens to H5DNA-HA vaccine using different promoters. Six groups of ten chickens each were immunized on day 0 with the indicated amount of either pCMV or pβ-actin HA5 DNA by particle-mediated delivery (gene gun) to the abdominal epidermis. On day 28 all chickens were challenged intranasally with 100 $LD_{50}$ of A/Ty/Ire/83. Protection was measured on the basis of survival from lethal infection. None of the survivors showed signs of influenza. All controls died of lethal infection within 5–7 days of challenge.
Figure 3A:
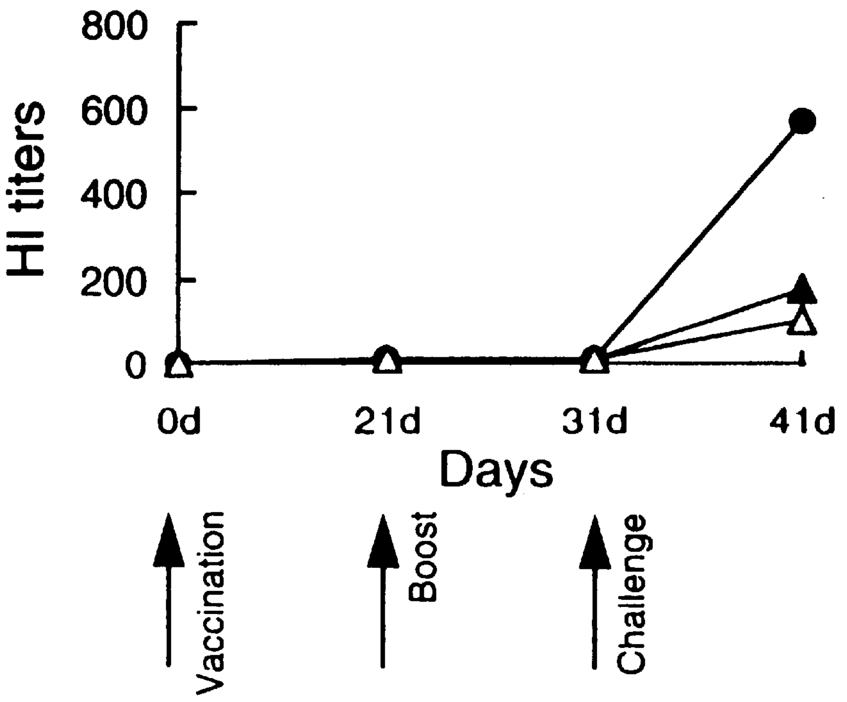
Figure 3B:
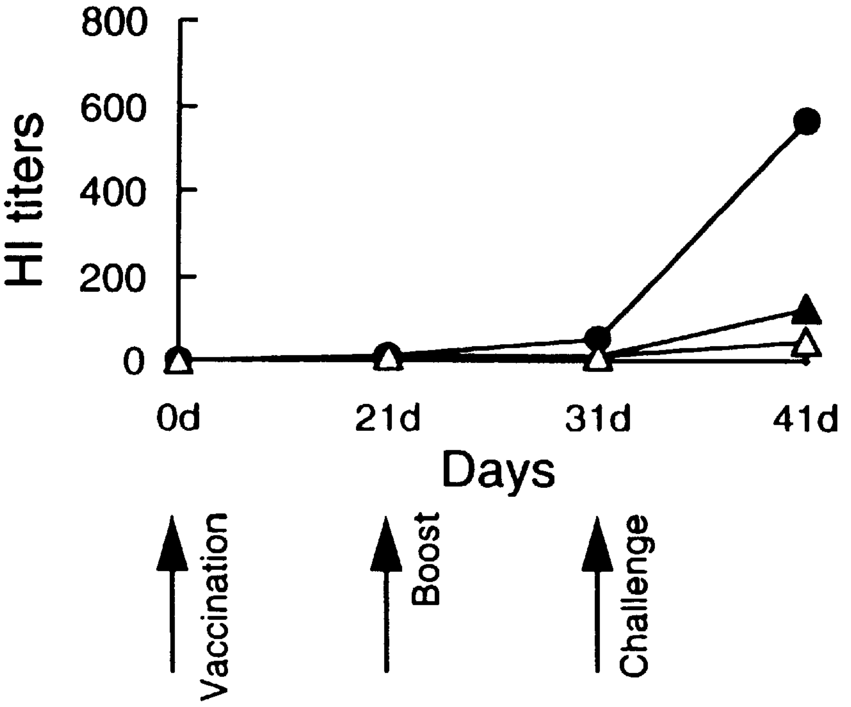
FIGS. 3B, 3D and 3F depict the results following the vaccination of the chickens with the inactivated whole virus vaccine.
Figure 3C:
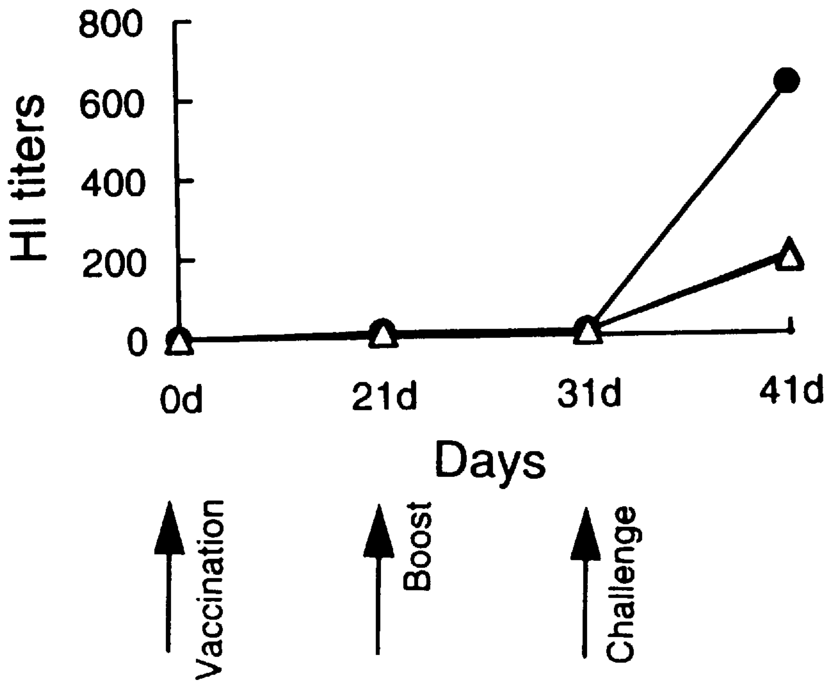
Figure 3D:
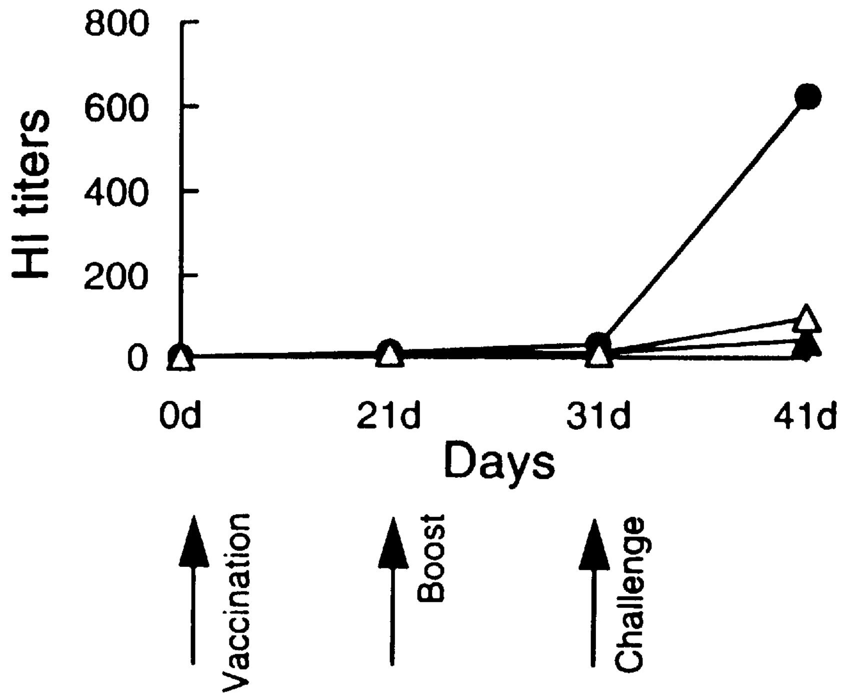
Figure 3E:
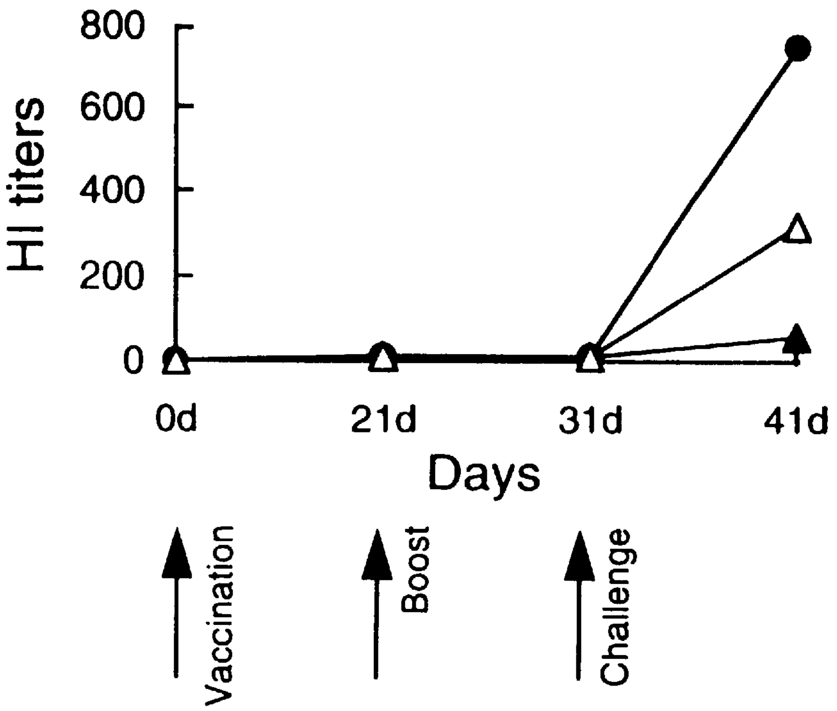
Figure 3F:
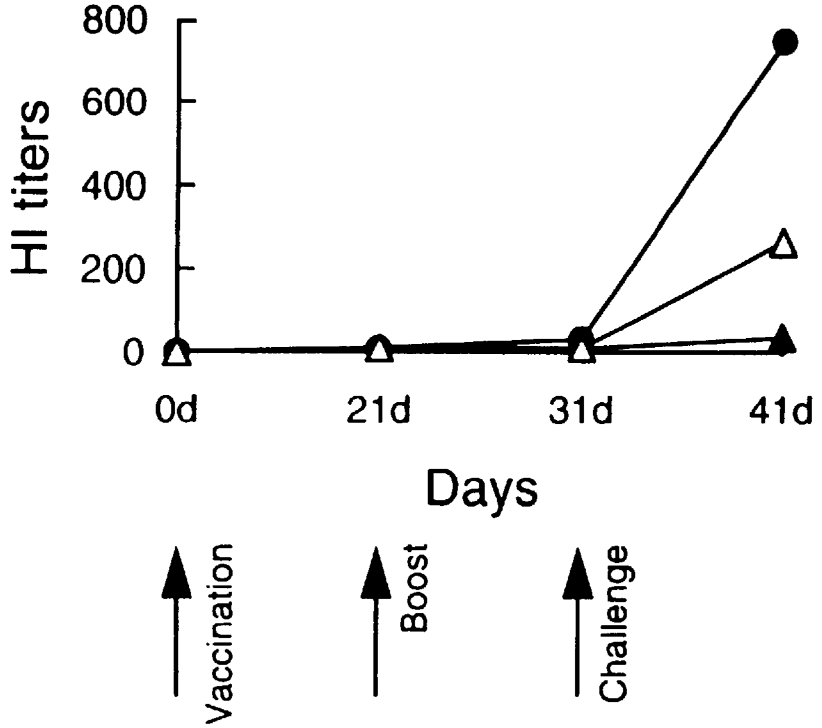

Dose-response curve for as H5 gene vaccine with different promnoters. To investigate the relationship between the amount of plasmid DNA administered by gene gull and the magnitude of the immune response, we vaccinated groups of 10 chickens each with various doses of pCMV-H5 or pβ-actin/H5 vector and measured the protective efficacy against lethal homologous challenge. With pCMV-H5, a dose of 0.25 μg of DNA protected 50% of the birds whereas a 1 μg dose protected 70%, a 5 μg dose protected 83%, and a 10 μg dose of DNA protected 100% of the birds. In comparison, 100% of the chickens were protected with doses of the pβ-actin-HA vaccine of 1 μg DNA or greater (FIG. 2).

Protection and cross-protection induced by the PCMV-HA vector. Vaccine efficacy for influenza virus is ultimately determined not only by efficacy for homologous virus but efficacy for antigenic drift. Therefore the extent of protection conferred by gene gun inoculated DNA against a challenge with either homologous H5 virus or an antigenic variant was determined.

Gene gun immunization of birds with 10 μg of pCMV/H5 DNA provided complete protection (9/9 birds) after a challenge with homologous virus (Ty/Ire/83) with no evidence of virus shedding in either the trachea or cloaca (Table 2). The same dose of DNA administered by gene gun also provided complete cross protection against challenge with the Ck/Penn/83 variant and 90% protection against Ck/Quert/95, again in the absence of virus shedding. Essentially the same results were obtained with 10 μg of HA inactivated whole virus vaccine, except that one chicken challenged homologously with Ty/Ire/83 continued to shed virus in the trachea (Table 2). None of the control chickens (given 10 μg of pCMV control DNA) survived their infections. Although 100% of the control chickens challenged with Ty/Ire/83 died, only 20% of them shed virus in their cloaca.

Of the 29 chickens vaccinated with H5-DNA only two became sick (including one death), compared with four of the 30 given the whole virus vaccine (including three deaths). Thus, the DNA vaccine was somewhat more efficacious than the conventional vaccine, affording high levels of protection against homologous H5 virus and its antigenic variants.

TABLE 2

Protection of chickens against antigenic variants of lethal H5 influenza challenge virus with either pCMV/H5 or inactivated whole-virus vaccine

| | | | Virus shedding at 3 days post infection | | | |
|---|---|---|---|---|---|---|
| | | | Trachea | | Cloaca | |
| Vaccine (dose: 10 μg) | Challenge virus | No. that survive/ no. tested[a] | No. of chickens shedding/ Total | Mean Virus[b] titer ($log_{10}EID_{50}$) | No. of chickens shedding/ Total | Mean Virus[b] titer ($log_{10}EID_{50}$) |
| DNA | Ty/Ire/83 | 9/9 | 0/9 | — | 0/9 | — |
| pCMV-HA | Ck/Penn/83 | 10/10 | 0/10 | — | 0/10 | — |
| | Ck/Quert/95 | 9/10[c] | 0/10 | — | 0/10 | — |
| DNA | Ty/Ire/83 | 0/10 | 8/10 | 3.6 | 2/10 | 2.8 |
| controls | Ck/Penn/83 | 0/10 | 10/10 | 3.1 | 8/10 | 2.5 |

TABLE 2-continued

Protection of chickens against antigenic variants of lethal H5 influenza challenge virus with either pCMV/H5 or inactivated whole-virus vaccine

| Vaccine (dose: 10 μg) | Challenge virus | No. that survive/ no. tested[a] | Virus shedding at 3 days post infection: Trachea: No. of chickens shedding/ Total | Trachea: Mean Virus[b] titer ($log_{10}EID_{50}$) | Cloaca: No. of chickens shedding/ Total | Cloaca: Mean Virus[b] titer ($log_{10}EID_{50}$) |
|---|---|---|---|---|---|---|
| pCMV | Ck/Quert/95 | 0/10 | 10/10 | 3.3 | 9/10 | 3.1 |
| Inactivated | Ty/Ire/83 | 8/10 (1) | 1/10 | 2.8 | 0/10 | — |
| whole-virus | Ck/Penn/83 | 9/10[c] | 0/10 | — | 0/10 | — |
| (Ty/Ire/83)[d] | Ck/Quert/95 | 10/10 (1) | 0/10 | — | 0/10 | — |

[a]Numbers in parentheses denote surviving chickens that became sick but recovered.
[b]The swabs were resuspended in 1 ml of isolation media and the mean virus titer is expressed as $log_{10}EID_{50}$/ml.
[c]Chickens died of infection prior to the collection of samples.
[d]Standardized per HA as described in Methods.

Antibody responses of chickens immunized with DNA and conventional vaccine. The relative abilities of formalin-inactivated and DNA vaccines to induce serum antibodies was also examined. Within the first 3 weeks post-immunization, no detectable antibodies were found in either vaccine group. However, in chickens given formalin-inactivated vaccine, vaccination with Ty/Ire/83 (on day 31) generated low levels of antibodies (GMT, 42) specific to the immunizing antigens. Antibodies to the Ck/Penn/83 or Ck/Quert/95 antigenic variant were not detected, nor did we find antibodies to any of the three H5 virus antigens used in booster immunization of the DNA vaccine group.

The profile of serum antibodies induced by homologous challenge was similar in both the DNA and whole virus vaccine groups (FIG. 3) and was characterized by high levels of HI antibodies specific to Ty/Ire/83 antigens. Serum antibody levels against the two antigenic variants, Ck/Penn/83 and Ck/Quert/95, did not differ substantially whether chickens were inoculated with HA-DNA or given the whole virus vaccine. They uniformly were threefold lower than antibody levels against homologous Ty/Ire/83 antigen.

The profile of serum antibodies induced by challenge with antigenic variants, Ck/Penn/83 and Ck/Quert/95, were similar in both the DNA and whole virus vaccine groups and were again characterized by high levels of HI antibodies being specific for Ty/Ire/83 antigen.

Discussion

In these studies, gene-gun delivery of DNA encoding the H5 hemagglutinin was shown to be an effective method of immunization in chickens. One hundred percent of the DNA-vaccinated chickens were protected against homologous challenge and 95% of the DNA-vaccinated chickens were protected against two H5 variants that otherwise cause lethal infection in chickens. This result was somewhat superior to that obtained with a standard inactivated whole virus vaccine. Furthermore, DNA vaccines allow viral infection to be ascertained in chickens prior to the detection of symptoms. Thus, agricultural workers do not have the problem of being unable to distinguish vaccinated avians from infected avians when a DNA vaccine is used. This is one major advantage of the use of a DNA vaccine that encodes a single antigen over the use of inactivated whole virus vaccines that contain essentially all of the antigens of the live virus.

The extent of protection correlated well with the amount of HA-DNA administered, for both pCMV and a chicken pβ-actin promoter transcription units. On a per μg of DNA basis, the β-actin promoter proved to be somewhat superior to the CMV promoter.

Antigenic determinants of the H5 variants. Booster vaccination (31 days) in the inactivated vaccine group generated low levels of antibodies to the immunizing antigen but none to the antigenic variants, suggesting critical differences among the three H5 viruses used in the present study [Kodihalli et al., *J. Virol*, 69:4888–4898 (1995)]. High levels of post-challenge antibody response to the priming antigen was observed in both the inactivated and DNA-immunized chickens, irrespective of the challenge antigen. This recall memory response to the priming antigen has been termed "original antigenic sin", in which the response to challenge depends not only on the nature of the challenge antigen but also its antigenic relatedness to priming antigen. Our previous studies (Kodihalli, 1995, supra), (Katz, 1989, supra) indirectly addressed this issue, showing that close antigenic relatedness between the priming and challenging antigen is responsible for the greater immunogenicity of challenge antigen if it is very closely related to the primary antigen (Kodihalli, 1995, supra). From our analysis of the H5 variants (Table 1), it is likely that increased antibody responsiveness to Ty/Ire/83 is due to antigenic differences between the priming (Ty/Ire/83) and the challenge antigens (Ck/Penn/83 and Ck/Quert/95). Whatever the explanation, vaccination with Ty/Ire DNA is sufficient to induce protective cross-reacting antibodies against antigenic variants.

Immunity induced by DNA vaccines is somewhat superior to that afforded by inactivated vaccine. Few published studies have addressed the range of protection induced by DNA vaccines compared with conventional inactivated virus vaccines (Donnelly, 1995, supra), (Justewicz, 1995, supra). Donnelly et al. (Donnelly, 1995, supra) demonstrated in ferrets that DNA vaccines encoding the HA and internal proteins are more effective against antigenic variants than either inactivated or subunit vaccine. Other investigators, using a murine model to analyze the effects of vaccine or antibody-producing B cells, found fewer antigen-specific B cells in mice vaccinated with subunit vaccine (purified HA) compared to those vaccinated with live virus or DNA (Justewicz, 1995, supra). In the present study, the induction of cross-protection against antigenic variants was not unique to the DNA vaccine, rather, the kinetics of protection against homologous and antigenic variants were similar whether DNA or conventional vaccine was used. However, based on analysis of post-challenge antibody responses (41 days), the DNA vaccine induced slightly higher levels of cross-reacting antibodies against antigenic variants than did the formalin-inactivated vaccine, suggesting a difference in the priming of cross-reacting T and B cells by these two preparations.

Relation of the promoter to DNA vaccine efficacy. Proper selection of a promoter/enhancer element to drive the expression of transferred genes is critical to successful gene delivery. This choice depends upon both the target cell type and the functional design of the vector transcription unit (Harms, 1995, supra). Therefore two different vector transcription units were tested in order to reduce the variability in the magnitude of immune responses previously seen with use of DNA vaccines in chickens (Fynan, 1993B, supra), (Robinson, 1993, supra). Chicken beta-actin is a major component of the cytoskeleton and one of the most abundant proteins in many cell types [Ponte et al., *Nucl. Acid. Res.*, 12:1687–1696 (1984)]. Since the rate of transcription of an abundantly expressed gene is very high [Lee et al., *J. Mol. Biol.*, 188:173–183 (1986)], the beta-actin gene promoter is likely a potent transcriptional initiator in chicken cells and could be expected to enhance expression of the HA gene. This prediction was substantiated by results of the present study, which showed a survival of 100% of the chickens inoculated with the pβ-actin vector at a 1 μg or greater dose level, as compared to the 10 μg dose requirement for the pCMV vector. Surprisingly pβ-actin was not superior to pCMV in transfection studies in vitro, underscoring the complexity of gene expression in higher organisms and the risk of extrapolating in vitro transfection data to in vivo efficacy.

One of the perceived risks of DNA immunization is the integration of the injected plasmid into the host. Therefore the DNA homology between the plasmid and the host, as in the case here with β-actin, may be viewed as less desirable. Thus, despite the apparent greater efficiency of pβ-actin relative to pCMV, the latter vector may be the vector of choice in many instances. On the other hand, when the inoculated avian has a short projected lifetime, e.g., chicken "broilers" live for only 2 to 3 months, the problem of potential integration into the avian DNA is not a factor of concern. Finally, to avoid low or undetectable antibody titers due to transient transfections, it may be necessary to inoculate avians more than twice with large doses of the DNA transcription unit.

Need for protection against H5N2 infection in chickens. Vaccination of chickens with DNA offers a number of advantages over immunization with whole inactivated virus. Cellular immune responses induced by DNA vaccines have the potential to protect chickens against antigenic variants, although high doses of inactivated vaccine could afford the same level of protection as indicated by results of the present study. DNA vaccines are easier to manufacture than inactivated virus vaccine, far less costly and they prevent the spread of infection more effectively. In the present study, 13% of chickens vaccinated with inactivated whole virus vaccine shed virus after challenge, compared with only 6% of DNA-vaccinated chickens. Furthermore, plasmid DNA is not subject to the same selective pressures that cause antigen changes among in vitro-propagated viruses and would therefore be expected to yield highly reproducible results. Most important is the simplicity and relative ease with which one can manipulate the delivery system; thus, it is possible to improve DNA vaccines by incorporating additional genes against multiple subtypes (e.g., H4, H5, H7) into the plasmid including immuno-effectors such as a cytokine gene or another immune modulator, thus immunizing the host against many serotypes of influenza with one vaccination.

The following is a list of documents related to the above disclosure and particularly to the experimental procedures and discussions. These documents, and all others cited above, should be considered as incorporated by reference in their entirety.

Bachmann, M. F., T. M. Kundig, C. P. Kalberer, H. Hengartner, and R. M. Zinkernagel. 1994. How many specific B Cells are needed to protect against a virus? J. Immunol. 152:4236–4241.

Bean et al., J. Virol., 54: 151–160 (1985)

Bos J. D., and M. L. Kapsenberg. 1993. The skin immune system: Progress in cutaneous biology. Immunology Today 14:75–78.

Chapman, B. S., R. M. Thayer, A. K. Vincent, and N. Haigwood. 1991. Effect of intron I from human cytomegalovirus (Towne) immediate-early gene on heterologous expression in mammalian cells. Nucle. Acids Res. 19:3979–3986.

Cohn, M., and R. E. Langman. 1990. The protection unit of humoral immnunity selected by evolution. Immunol. Rev. 115:7.

Conry, R. M., B. A. Lo, J. Kantor, J. Schlom, F. Loechel, S. E. Moore, L. A. Sumerel, D. L. Barlow, S. Abrams, and D. T. Curiel. 1994. Immune response to a carcinoembryonic antigen polynucleotide vaccine. Cancer Res. 54:1164–1168.

Cox, G. J., T. J. Zamb, and L. A. Babiuk.1993. Bovine herpesvirus immune responses in mice and cattle injected with plasmid DNA. J. Virol. 67:5664–5667.

Cullen, B. R. 1986. Trans-activation of human immunodeficiency virus occurs via a bimodel mechanism. Cell 46:973–982.

Davis, H. L., M. L Michel, and R. G. Whalen. 1993. DNA based immunization for hepatitis B induces continuous secretion of antigen and high levels of circulating antibody. Hum. Mole. Genet. 2:1847–1851.

Donnelly, J. J. A. Friedman, D. Martinez, D. L. Montgomery, J. W. Shiver, S. H. Motzel, J. B. Ulmer, M. A. Liu. 1995. Preclinical efficacy of a prototype DNA vaccine: Enhanced protection against antigenic drift in influenza virus. Nat. Medicine 6:583–587.

Easterday, B. C., and V. S. Hinshaw. 1991. Influenza. Disease of Poultry (B. W. Calneck, Ed.) 9th ed., pp 532–551. Iowa State Univ.Press, Ames, Iowa.

Eisenbraun, M. D., D. H. Fuller, and J. R. Haynes. 1993. Examination of parameters affecting the elicitation of humoral immune responses by particle bombardment-mediated genetic immunization. DNA Cell Biol. 12:791–797.

Fynan, E. F., H. L. Robinson, and R. G. Webster. 1993A. Use of DNA encoding influenza hemagglutinin as an avian influenza vaccine. DNA Cell Biol. 12:785–789.

Fynan, E. F., R. G. Webster, D. H. Fuller, J. R. Haynes, J. C. Santoro, and H. L. Robinson. 1993B. DNA vaccines: protective immunizations by parenteral, mucosal, and gene-gun inoculations. Proc. Natl. Acad. Sci. USA 90:11478–11482.

Halvorson, D. A., S. Kodihalli, E. Laudert, J. A. Newman, B. S. Pomeroy, D. Shaw, and V. Sivanandan. 1992. Influenza in turkeys in U.S.A. (1987–1991). Proceedings of the Third International Symposium on Avian Influenza, pp.33–42. University of Wisconsin-Madison, Wis.

Harms, J. S., and G. A. Splitter. 1995. Interferon -$_m$ inhibits transgene expression driven by SV 40 or CMV promoters but augments expression driven by the mammalian MHC I promoter. Human Gene Ther. 6:1291–1297.

Gerhard, W. 1978. The analysis of the monoclonal immune response to influenza virus. III. The relationship between stimulation of virus primed precursor B-cells by heterologous virus and reactivity of selected antibodies. J. Immunol. 120(4):1164–1168.

Justewicz, D. M., P. C. Doherty, and R. G. Webster. 1995. The B-cell response in lymphoid tissue of mice immunized with various antigenic forms of influenza virus hemagglutinin. J.Virol. 69:5414–5421.

Katz, J. M., and R. G. Webster. 1989. Efficacy of inactivated influenza A virus(H3N2) vaccine grown in mammalian cells or in embryonated egg. J.Infect.Dis. 160:191–198.

Kawaoka, Y., C. W. Naeve, and R. G. Webster. 1984. Is virulence of H5N2 influenza viruses in chickens associated with loss of carbohydrate from the hemagglutinil? Virology 139:303–316.

Kawaoka, Y., I. Nestorowicz, D. J. Alexander, and R. G. Webster. 1987. Molecular analysis of hemagglutinin genes of H5 influenza viruses: Origin of a virulent turkey strain. Virology 158:218–227.

Kawaoka, Y., and R. G. Webster. 1988. Sequence requirements for cleavage activation of influenza virus hemagglutinin expressed in mammalian cells. Proc.Natl. Acad-.Sci. USA 85:324–328.

Kodihalli, S., D. M. Justewicz, L. Gubareva, and R. G. Webster. 1995. Selection of a single amino acid substitution in the hemagglutinin molecule by chicken eggs can render influenza I virus (H3) vaccine candidate vaccine ineffective. J. Virol. 69: 4888–4898.

Laver, W. G. 1969. Purification of influenza virus, pp 82–86. In K. Habel and N. P Salzman (ed.), Fundamental techniques in virology, Academic Press, Inc., New York.

Lee, J. J., F. L. Calzone, R. J. Britten, R. C. Angerer, and E. H. Davidson. 1986. Activation of sea urchin actin genes during embryogenesis: measurement of transcript accumulation from five different genes in *Strongylocentrotus purpuratus*. J.Mol. Biol. 188:173–183.

Michel, M. L., H. L. Davis, M. Schleef, M. Mancini, P. Tiollais, and R. G. Whalen. 1995. DNA-mediated immunization to the hepatitis B surface antigen in mice: Aspects of the humoral response mimic hepatitis B viral infection in humans. Proc. Natl. Acad. Sci. USA 92:5307–5311.

Montgomery, D. L., J. W. Shiver, K. R. Leander, H. C. Perry, A. Friedman, D. Martinez, J. B. Ulmer, J. J. Donnelly, and M. A. Liu. 1993. Heterologous and homologous protection against influenza A by DNA vaccination: optimization of DNA vectors. DNA Cell Biol. 12:777–783.

Niwa, H., K. Yamamura, and J. Miyazaki. 1991. Efficient selection for high-expression transfectants with a novel eukaryotic vector. Gene 108:193–200.

Ponte, P., S. Ng, J. Engle, P. Gunning, and L. Kedes. 1984. Evolutionary conservation in the untranslated regions of actin mRNAs: DNA sequence of a human β-actin cDNA. Nucl. Acid. Res. 12:1687–1696.

Raz, E., D. A. Carson, S. E. Parker, T. B. Parr, A. M. Abai, G. Aichinger, S. H. Gromkowski, M. Singh, D. Lew, M. A. Yankauckas, S. M. Baird, and G. H. Rhodes. 1994. Intradermal gene immunization: The possible role of DNA uptake in the induction of cellular immunity to viruses. Proc. Natl. Acad. Sci. USA 91:9519–9523.

Robinson, H. L., L. A. Hunt, and R. G. Webster. 1993. Protection against a lethal influenza virus challenge by immunization with a hemagglutinin-expressing plasmid DNA. Vaccine 11:957.

Sedegah, P. and S. Hoffman. 1994. Protection against malaria achieved by DNA immunization. Proc. Natl. Acad. Sci. USA 91:9866–9870.

Stingl, G. 1990. Dentritic cells of the skin. Dermatol. Clin. 8:673–679.

Stingl G, E. T Schachler, V. Groh, K.Wolff , and Hauser III 1989. The immune functions of epidermal cells. Immunol. Ser. 4:3–72.

Taylor, J., G.Weinberg, Y. Kawaoka, R.G. Webster, and E. Paoletti. 1988. Protective immunity against avian influenza induced by a fowlpox virus recombinant. Vaccine 6:504–508., Ulmer, J. B., J. J. Donnelly, S. E. Parker, G. H. Rhodes, P. L. Feigner, V. J. Dwarki, S. H. Gromkowski, R. R. Deck, C. M. DeWitt, A. Friedman, L. A. Hawe, K. R. Leander, D. Martinez, H. C. Perry, J. W. Shiver, D. L. Montgomery, and M. A. Liu.1993. Heterologous protection against influenza by injection of DNA encoding a viral protein. Science 259:1745–1749.

Wang, B., K. E. Ugen, V. Srikantan, M. G. Agadjanyan, K. Dang, Y. Refaeli, A. I. Sato, J. Boyer, W. V. Williams, and D. B. Weiner. 1993. Gene inoculation generates immune responses against human immunodeficiency virus type 1. Proc. Natl. Acad. Sci. USA 90:4156–4160.

Webster R. G., E. F. Fynan, J. C. Santro and H. L Robinson. 1994. Protection of ferrets against influenza challenge with a DNA vaccine to hemagglutinin. Vaccine 12:1495–1498.

WHO Collaborating Center for Reference and Research on influenza. 1982. Concepts and procedures for laboratory based influenza surveillance,B-19,WHO Collaborating Center for Reference and Research on influenza, Center for Disease Control, Atlanta.

Wood , J. M., Y. Kawaoka, L. A. Newberry, E. Bordwell, and R. G. Webster. 1985. Standardization of inactivated H5N2 influenza vaccine and efficacy against lethal A/Chicken/Pennsylvania/1370/83 infection. Avian. Dis. 29:867–872.

Xiang, Z.Q, L. Spitalnic, J. Cheng, J. Erickson, B. Wojczyk, and H. C. J. Ertl. 1995. Immune response to nucleic acid vaccines to rabies virus. Virology 209:564–579.

Xiang, Z.Q., S. Spitalnik, M. Tran, W. H. Wunner, J. Cheng, and H. C. J. Ertl. 1994. Vaccination with a plasmid vector carrying the rabies virus glycoprotein gene induces protective immunity against rabies virus. Virology 199:132–140.

Yankauckas, M. A., J. E. Morrow, S. E. Parker, I. Abai, G. H. Rhodes, V. J. Dwaraki, and S. H. Gromkowski. 1993. Long-term anti-nucleoprotein cellular and humoral immunity is induced by intramuscular injection of plasmid DNA containing NP gene. DNA Cell Biol. 12:771–776.

While the invention has been described and illustrated herein by references to the specific embodiments, various specific material, procedures and examples, it is understood that the invention is not restricted to the particular material combinations of material, and procedures selected for that purpose. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications in addition to the immediately foregoing are cited herein, the disclosures of which are incorporated by reference in their entireties. The citation of any reference herein should not be deemed as an admission that such reference is available as prior art to the instant invention.

What is claimed is:

1. A method of immunizing an avian by eliciting a protective immune response from an influenza virus subtype comprising administering to the avian an effective quantity of a vector comprising a DNA transcription unit that comprises a nucleic acid operatively linked to a DNA promoter;

wherein the vector is neither a live nor an attenuated virus;

wherein the nucleic acid encodes an antigen from the influenza virus subtype; and wherein the vector comprising the DNA transcription unit is administered by a gene gun.

2. The method of claim 1 wherein the antigen is a hemagglutinin.

3. The method of claim 2 wherein said protective immune response successfully leads to the survival of the avian in greater than 95% of the cases in which the avian is challenged intranasally with 100 $LD_{50}$ of the influenza virus subtype.

4. The method of claim 3 wherein the avian is selected from the group consisting of a chicken and a turkey.

5. The method of claim 4 wherein the avian is a chicken and the influenza virus subtype is H5.

6. The method of claim 5 wherein the DNA promoter is a cytomegalovirus immediate early promoter.

7. The method of claim 5 wherein the DNA promoter is an avian beta-actin promoter.

8. The method of claim 1 wherein the amount of DNA administered is between 0.75 to 12 $\mu$g.

9. A method of immunizing an avian ag,ainst more than one subtype of influenza virus by eliciting a protective immune response from more than one influenza virus subtype comprising administering to the avian an effective quantity of a first vector and an effective quantity of a second vector; wherein the neither the first vector nor the second vector is a live or an attenuated virus;

wherein the first vector comprises a DNA transcription unit comprising a first nucleic acid operatively linked to a DNA promoter; wherein said first nucleic acid encodes a first antigen from a first influenza virus subtype; and wherein the second vector comprises a DNA transcription unit that comprises a second nucleic acid operatively linked to a DNA promoter; wherein the second nucleic acid encodes a second antigen from a second influenza virus subtype; and wherein administering to the avian an effective quantity of the first vector is performed with a gene gun.

10. The method of claim 9 wherein the first influenza subtype is H5, and the second influenza subtype is H7.

11. The method of claim 10 wherein the first antigen is H5 hemagglutinin and the second antigen is H7 hemagglutinin.

12. A method of immunizing an avian against more than one subtype of influenza virus by eliciting a protective immune response from one or more influenza virus subtypes comprising administering to the avian an effective quantity of a vector comprising a DNA transcription unit that comprises a nucleic acid encoding at least two antigens, wherein the nucleic acid is operatively linked to one or more DNA promoters;

wherein the vector is not a live or an attenuated virus;

wherein at least two of said different antigens are derived from different influenza virus subtypes; and wherein administering to the avian an effective quantity of the vector is performed with a gene gun.

13. The method of claim 12 wherein said protective immune response leads to the survival of the avian in greater than 75% of the cases in which the avian is challenged intranasally with 100 $LD_{50}$ of any two of said different influenza virus subtypes.

14. The method of claim 13 wherein the nucleic acid encodes more than two different antigens and wherein said protective immune response leads to the survival of the avian in greater than 75% of the cases in which the avian is challenged intranasally with 100 $LD_{50}$ of all of said different influenza virus subtypes.

15. The method of claim 12 wherein at least one of the antigens is a hemagglutinin.

16. A method of immunizing an avian by eliciting a protective immune response from a non-lethal influenza virus subtype comprising administering to the avian an effective quantity of a vector comprising a DNA transcription unit that comprises a nucleic acid operatively linked to a DNA promoter;

wherein the vector is neither a live nor an attenuated virus;

wherein the nucleic acid encodes an antigen from the non-lethal influenza virus subtype; and wherein the vector comprising the DNA transcription unit is administered by a gene gun.

17. The method of claim 16 wherein said protective immune response successfully leads to the protection of the avian from infection in greater than 95% of the cases in which the avian is challenged intranasally with 100 $ID_{50}$ of the non-lethal influenza virus subtype.

18. A method of immunizing a chicken by eliciting a protective immune response from an influenza virus subtype comprising administering to the chicken an effective quantity of a vector comprising a DNA transcription unit that comprises a nucleic acid operatively linked to a DNA promoter;

wherein the vector is neither a live nor an attenuated virus; and wherein the nucleic acid encodes an hemagglutinin from the H5 influenza virus subtype.

19. The method of claim 18 wherein the DNA promoter is selected from the group consisting of a cytomegalovirus immediate early promoter and an avian beta-actin promoter.

20. The method of claim 18 wherein said administering is performed through a route selected from the group consisting of parenterally, intravenously, intraperitoneally, intradermally, subcutaneously, and intramuscularly.

21. The method of claim 18 wherein the vector comprising the DNA transcription unit is administered by a gene gun.

22. The method of claim 18 wherein the amount of DNA administered is 200 $\mu$g.

23. A DNA transcription unit comprising a nucleic acid encoding a hemagglutinin from a first influenza virus subtype H5 operatively linked to an avian beta-actin promoter.

24. The DNA transcription unit of claim 23 further comprising a nucleic acid encoding a second hemagglutinin from a second influenza virus subtype also operatively linked to a DNA promoter.

* * * * *